United States Patent [19]

Dannhardt et al.

[11] Patent Number: 5,260,451
[45] Date of Patent: Nov. 9, 1993

[54] SUBSTITUTED PYRROLE COMPOUNDS AND USE THEREOF IN PHARMACEUTICAL COMPOSITIONS

[75] Inventors: Gerd Dannhardt, Eschborn; Ludwig Steindl; Matthias Lehr, both of Munich, all of Fed. Rep. of Germany

[73] Assignees: Merckle GmbH; G. Dannhardt, both of Fed. Rep. of Germany

[21] Appl. No.: 886,396

[22] Filed: May 21, 1992

Related U.S. Application Data

[63] Continuation of Ser. No. 521,402, May 10, 1990, abandoned.

[30] Foreign Application Priority Data

May 11, 1989 [DE] Fed. Rep. of Germany ....... 3915450

[51] Int. Cl.$^5$ .................... C07D 471/04; A61K 31/41
[52] U.S. Cl. .................................................. 548/453
[58] Field of Search .................... 548/453; 514/413

[56] References Cited

U.S. PATENT DOCUMENTS

| 3,705,905 | 12/1972 | Culvenor et al. | 548/453 |
| 4,284,562 | 8/1981 | Anderson et al. | 548/562 |
| 4,327,221 | 4/1982 | Wei | 548/154 |
| 4,560,699 | 12/1985 | Muchowski et al. | 514/513 |

FOREIGN PATENT DOCUMENTS

| 0043858 | 1/1982 | European Pat. Off. |
| 0091181 | 10/1983 | European Pat. Off. |
| 0118321 | 9/1984 | European Pat. Off. |
| 0147317 | 7/1985 | European Pat. Off. |
| 0203787 | 12/1986 | European Pat. Off. |
| 0252823 | 1/1988 | European Pat. Off. |
| 0297987 | 1/1989 | European Pat. Off. |
| 1940551 | 6/1970 | Fed. Rep. of Germany. |
| 2062984 | 6/1972 | Fed. Rep. of Germany. |
| 2261965 | 6/1973 | Fed. Rep. of Germany. |
| WO82/02044 | 6/1982 | PCT Int'l Appl. |
| 1156477 | 6/1969 | United Kingdom. |

OTHER PUBLICATIONS

G. Dannhardt, R. Obergrusberger, 2,3-Dihydro-1-H-pyrrolizine, Archiv der Pharmazie, vol. 312, No. 1 (Jan. 1979) at 896.

(List continued on next page.)

Primary Examiner—David B. Springer
Attorney, Agent, or Firm—Bacon & Thomas

[57] ABSTRACT

The invention concerns substituted pyrrole compounds and their pharmaceutical applications. The compounds of the invention are potent inhibitors of lipoxygenase and cyclo-oxygenase and therefore are suitable to treat the set of rheumatic illnesses and to prevent allergically induced ailments. The compounds have the general formula:

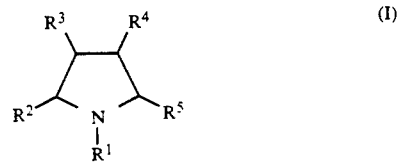

where $R^1$ denotes a $C_1$-$C_{12}$ alkyl group, $R^2$ denotes a hydrogen atom or a $C_1$-$C_{12}$ alkyl group, or $R^1$ and $R^2$ together with the carbon atom and the nitrogen atom to which they are bound form a ring of 5 to 8 links which may contain a sulfur heteroatom or a carbonyl group and may be substituted with one or two $C_1$-$C_4$ alkyl groups, each time two of the residues $R^3$, $R^4$ and $R^5$ independently from one another represent a hydrogen atom, a $C_5$-$C_8$ cycloalkyl group, a $C_1$-$C_{12}$ alkyl group or an aryl group which may be substituted by one or two residues selected from a halogen atom, a nitro-, a $C_1$-$C_4$ alkoxy-, a hydroxy-, a $C_1$-$C_4$ alkyl- or phenoxy-group, and where the third of the residues $R^3$, $R^4$ and $R^5$ denotes —CHO, —CO$_2$H, —COSC$_1$-C$_4$-alkyl or A—X, with A being a straight-chain or a branched $C_1$-$C_8$ alkylene group which may be interrupted by an oxygen heteroatom or a carbonyl group or being a $C_2$-$C_8$ alkenylene group, X being CO$_2$H, SO$_3$H, CHO, OH or SH, as well as their pharmaceutically compatible salts and esters, for pharmaceutical applications.

8 Claims, No Drawings

OTHER PUBLICATIONS

G. Dannhardt, L. Steindl, Antiinflammatory 2,3-dihydro-1H-Pyrrolizines. II: Addition of 6,7-diphenyl-2,3-dihydro-1H-pyrrolizine to Dimethyl Acetylenedicarboxylate and Diethyl Azodicarboxylate, Heterocycles, vol. 23, No. 5 (1985) at 1219.

G. Dannhardt, L. Steindl, Aminomethylierung und Arylthiolierung von 6.7-Diaryl-2.3-dihydro-1H-pyrrolizinen, Archiv der Pharmazie, vol. 319 (1986) at 65.

G. Dannhardt, L. Steindl, Oxidative Ringöffnung von 6.7-Diphenyl-2.3-dihydro-1H-pyrrolizin (DADHP) durch m-Chlorperbenzoesäure, Archiv der Pharmazie, vol. 319 (1986) at 231.

G. Dannhardt, L. Steindl, Synthese von 3-(6.7-Diphenyl-2.3-dihydro-1H-pyrrolizin-5-yl)-propionäure, Archiv der Pharmazie, vol. 319 (1986) at 234.

G. Dannhardt, L. Steindl, Natriummetaperiodat-Oxidation von 6.7-Diphenyl-2.3-dihydro-1H-pyrrolizin, Archiv der Pharmazie, vol. 318 (1986) at 661.

G. Dannhardt, L. Steindl, 6.7-Diaryl-2.3-dihydro-1-H-pyrrolizine (DADHP) als Singulett-Sauerstoff-Fänger, Archiv der Pharmazie, vol. 318 (1985) at 663.

G. Dannhardt, L. Steindl, Zur Synthese und Decarboxylierung von 6.7-Diaryl-2.3-dihydro-1H-pyrrolizin-5-yl-essigsäure (DADHP-5-essigsäure), Archiv der Pharmazie, vol. 319 (1986) at 354.

G. Dannhardt, L. Steindl, Synthese und Oxidation von 6.7-Diphenyl-2.3-dihydro-1H-pyrrolizin-5-yl-acetaldehyd (DADHP-5-acetaldehyd), Archiv der Pharmazie, vol. 319 (1986) at 500.

G. Dannhardt, L. Steindl, 6.7-Diarylsubstituierte 1- und 3-Pyrrolizinone (1-DAPON und 3-DAPON), Archiv der Pharmazie, vol. 319 (1986) at 749.

V. G. Dannhardt, L. Steindl, Dihydropyrrolizinyl-substituierte 2-Aminoethanol- und Glykolsäure-Derivate, Chemiker-Zeitung, vol. 110, No. 3 (1986) at 124.

V. G. Dannhardt, M. Lehr, L. Steindl, Carbaldehyde und hydroxymethylierte Derivate stellungsisomerer Diaryl-2,3-dihydro-1H-pyrrolizine (5,6-, 5,7- und 6,7-DADHP-Derivate, Chemiker-Zeitung, vol. 110, No. 7/8 (1986) at 267.

G. Dannhardt, M. Lehr, Stellungsisomere Diaryldihydropyrrolizinyl-essigsäuren und- hydroxyethyl-Derivate, Archiv der Pharmazie, vol. 321, No. 6 (1988) at 159.

G. Dannhardt, M. Lehr, Stellungsisomere Diaryldihydropyrrolizinyl-ameisensäuren und- propionsäuren, Archiv der Pharmazie, vol. 321 (1988) at 545.

G. Dannhardt, M. Lehr, Diaryldihyderopyrrolizincarbonsäuren und N-alkyldiarylpyrrolcarbonsaäuren als Inhibitoren von 5-lipoxygenase und cyclooxygenase, Scientia Pharmaceutica, vol. 56 (1988) at 7.

I. Lalezari, E. L. Schwartz, Synthesis and Antineoplastic Activity of 5-Aryl-2,3-dihydropyrrolo[2,1-b]-thiazole-6,7-dimethanol 6,7-Bis(isopropylcarbamates), J. Med. Chem., vol. 31 (1988) at 1427.

T. Pyl, H.-D. Dinse, O. Sietz, Über bicyclisch Heterocyclen mit gemeinsamem Sticksoffatom, VII, Liebigs Ann. Chem., vol. 676 (1964) at 141.

T. Thielmann, M. Güntert, M. Köpsel, P. Werkhoff, Synthesis of 1H-pyrrolo-[1,2-c]-[1,3]-Thiazine: A New Sulphur-Nitrogen Heterocycle, Tetrahedron Letters, vol. 30, No. 34 (1989) at 4507.

W. Flitsch, E. Mukidjam, Beiträge zur Chemie der Cycl[4.3.2]azine, Chem. Ber., vol. 112 (1979) at 3577.

J. C. Brindley, D. G. Gillon, G. D. Meakins, Routes to Pyrrolo[2,1-b]thiazoles, Rotational Isomerism of Pyrrolo[2,1-b]-thiazole-5-carbadehydes, J. Chem. Soc. Perkin Trans. I (1986) at 1255.

B. Molloy, D. H. Reid, F. S. Skelton, Studies of Heterocyclic Compounds. Part I. A Synthesis of 6-Substituted Pyrrolo[2,1-b]thiazoles, Dept. of Chem., The Univ., St. Andrews, (1965) at 65.

J. M. Muchowski, D. R. Solas, Lithiation of pyrrole-2-acetic acids, 171016T Chem. Abstr., vol. 101 (1984) at 681.

J. M. Brittain, R. A. Jones, J. S. Arques, T. A. Saliente, Utilization of 1-methyl-2-pyrrolyllithium in the synthesis of 1-methyl-2-substituted pyrroles, 96: 217628c Chem. Abstr., vol. 96, (1982) at 722.

H. Carpio, E. Galeazzi, R. Greenhouse, A. Guzman, E. Velarde, Y. Antonio, F. Franco, A. Leon, V. Perez et al., Synthesis of 1,2-dihydro-3H-pyrrolo[1,2-a]pyrrole-1-carboxylic acids and homologous pyridine and azepine analogs thereof, 98A: 4471A Chem. Abstr., vol. 98 (1983) at 401.

Patent Abstract of AU-A-18880/88, (Jan. 1989), Australian Patent Office.

J. of Med. Chem., vol. 30, No. 5 (1987) at 821.

SUBSTITUTED PYRROLE COMPOUNDS AND USE THEREOF IN PHARMACEUTICAL COMPOSITIONS

This application is a continuation of application Ser. No. 07/521,402, filed May 10, 1990, now abandoned.

The invention concerns substituted pyrrole compounds and their applications to pharmacy and to drugs containing these compounds.

It is known that arachidonic acid metabolizes two different ways. In the cyclooxygenase way the cyclooxygenase enzyme metabolizes the arachidonic acid into prostaglandins. In the lipoxygenase way, the arachidonic acid affected by the lipoxygenases is metabolized into the so-called leucotrienes.

The prostaglandins take part in the generation of inflammation, fever and pain, whereas the leucotrienes are significant in the generation of asthma, inflammations and allergies. Frequently non-steroidal antiphlogistics such as derivatives of arylacetic-acid, 2-aryl-propionic-acid and anthranilic acid to fight those symptoms. These derivatives inhibit cyclo-oxygenase and thereby prevent the formation of prostaglandins from arachidonic acid. However the use of such derivatives is questionable on account of their side effects. On the other hand, drugs inhibiting lipoxygenase are not commercially available.

Now it was found in surprising manner that certain substituted pyrrole compounds are potent cyclo-oxygenase and/or lipoxygenase inhibitors and therefore are suitable to prevent allergically induced maladies and to treat the set of rheumatic illnesses.

Accordingly the object of the invention are substituted pyrrole compounds of the general formula I

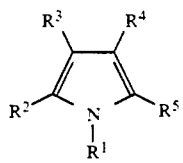

where
$R^1$ denotes a $C_1$-$C_{12}$ alkyl group,
$R^2$ is a hydrogen atom or a $C_1$-$C_{12}$ alkyl group, or
$R^1$ and $R^2$ together with the carbon atom and the nitrogen atom to which they are bound form a 5- to 8- link ring which also may contain a sulfur heteroatom or a carbonyl group and which where called for may be substituted with one to two $C_1$-$C_4$ alkyl groups,
each time, two of the residues $R^3$, $R^4$ and $R^5$ independently of each other are a hydrogen atom, a $C_5$-$C_8$ cycloalkyl group, a $C_1$-$C_{12}$ alkyl group or an aryl group which may be substituted by one or two residues selected form a halogen atom, a nitro-, a $C_1$-$C_4$ alkoxy, hydroxy, a $C_1$-$C_4$ alkyl or phenoxy group, and
the third of the residues $R^3$, $R^4$ and $R^5$ denotes —CHO, —CO$_2$H, —COSC$_1$-C$_4$-alkyl or A—X, with A being a straight chain or branched $C_1$-$C_8$ alkylene group which may be interrupted by a hydrogen heteroatom or a carbonyl group, or a $C_2$-$C_8$ alkenyl group, and with X being CO$_2$H, SO$_3$H, CHO, OH or SH.

as well as their pharmaceutically compatible salts and esters, for application in pharmacy.

In the present case the pharmaceutically compatible salts may be salts of acid or of base addition. For acid addition salts, inorganic acids such as hydrochloric acid, sulfuric acid or phosphoric acid are used, or such organic acids as tartaric acid, lactic acid, citric acid, malic acid, mandelic acid, ascorbic acid, maleic acid, fumaric acid, gluconic acid and the like.

The base salts include the salts of the compounds of formula I with inorganic bases such as sodium or potassium hydroxide or with organic bases such as mono-, di- or tri-ethanolamine.

The esters of the compounds of formula I include in particular physiologically easily hydrolyzed esters such as alkyl-, pivaloyloxymethyl-, acetoxymethyl-, phthalidyl-, indanyl- and methoxymethyl-ester.

The term "alkyl, alkoxy etc." covers straight-chain or branched alkyl groups such as methyl, ethyl, n- and i-propyl, n-, i- or t-butyl, n-pentyl, neopentyl, n-hexyl etc.

Unless otherwise stated, "alkyl" preferably shall denote $C_1$-$C_8$ alkyl and in particular $C_1$-$C_6$ alkyl.

Preferably aryl shall denote naphthyl and in particular phenyl.

The expression "halogen atom" covers an atom of fluorine, chlorine, bromine or iodine, especially a fluorine or chlorine atom.

The cyclo-alkyl residue preferably denotes a cyclopentyl or cyclohexyl residue.

A preferred embodiment mode are compounds of the formula Ia:

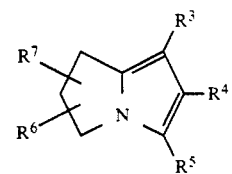

where $R^3$, $R^4$ and $R^5$ are the same as stated above in relation to formula I and where $R^6$ and $R^7$ independently from one another denote a hydrogen atom or a $C_1$-$C_4$ alkyl group.

Especially preferred compounds of formula Ia are those wherein two of the residues $R^3$, $R^4$ and $R^5$ denote a phenyl group which is possibly substituted by one or two residues selected from a halogen atom, in particular a fluorine or chlorine atom, from a $C_1$-$C_4$ alkyl-, $C_1$-$C_4$ alkoxy-, hydroxy- and phenoxy-group and where the third residue denotes A—X, with A being a $C_2$-$C_8$ alkylene group or a $C_1$-$C_8$ alkenylene group, and with X being CO$_2$H.

In particular AX denotes $C_2$-$C_6$-alkylene-CO$_2$H or $C_2$-$C_6$-alkenylene—CO$_2$H and in an especially preferred instance it stands for (CH$_2$)$_2$CO$_2$H, CH$_2$CO$_2$H or CH=CH CO$_2$H.

Preferably $R^6$ and $R^7$ are in the 2-position of the pyrrolizine structure and in particular they designate both a hydrogen atom or a methyl group.

Especially preferred embodiment modes are the compounds of the formulas

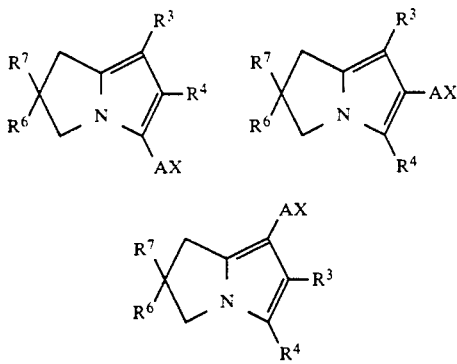

where $R^6$ and $R^7$ denote a hydrogen atom or a $C_1$–$C_4$ alkyl group and $R^3$ and $R^4$ denote a phenyl group which may be substituted by one or two residues which are selected from a halogen atom, a nitro-, $C_1$–$C_4$ alkoxy-, $C_1$–$C_4$ alkyl- or a phenoxy-group. A—X has the same meaning as above in relation to the formula I.

Preferably the substituents of the phenyl group are selected from a halogen atom, in particular a fluorine or chlorine atom, from a $C_1$–$C_4$ alkyl-, $C_1$–$C_4$ alkoxy- and phenoxy-group. Preferably the substituents shall be in the m- and/or in the p-position.

Preferably A denotes a $C_2$–$C_8$ alkylene group or a $C_1$–$C_8$ alkenylene group in particular, or a $C_2$–$C_6$ alkylene- or $C_2$–$C_6$ alkenylene group and X preferably denotes $CO_2H$.

Another embodiment mode are the compounds of formula I
- where $R^1$ and $R^2$ independently of one another denote a $C_1$–$C_{12}$ group, with two of the residues $R^3$, $R^4$ and $R^5$ being a phenyl group possibly substituted by one or two residues selected from a halogen atom, a $C_1$–$C_4$ alkyl-, $C_1$–$C_4$ alkoxy-, hydroxy- and phenoxy-group, and
- where the third of the residues $R^3$, $R^4$ and $R^5$ is a hydrogen atom or A—X, with A being a $C_1$–$C_6$ alkylene- or a $C_2$–$C_6$ alkenylene-group and X being $CO_2H$ or $SO_3H$.

$R^1$ preferably is a $C_1$–$C_8$ alkyl group, in particular a $C_1$–$C_6$ alkyl group and especially preferred a $C_4$–$C_6$ alkyl group.

$R^2$ preferably is a $C_1$–$C_4$ alkyl group and especially a methyl group.

$R^3$ and $R^4$ on one hand and $R^4$ and $R^5$ on the other preferably are a phenyl group and $R^5$ and $R^3$ resp. are A—X, with A being preferably a $C_1$–$C_4$ alkylene group or a $C_2$–$C_6$ alkenylene group. Especially preferred compounds are:
(2,2-dimethyl-6,7-diphenyl-2,3-dihydro-1H-pyrrolizine-5-yl)-acetic acid, and
3-(2,2-dimethyl-6-(4-phenoxyphenyl)-7-phenyl-2,3-dihydro-1H-pyrrolizine-5-yl) propionic acid.

Further the invention concerns the compounds of the general formula I and also the corresponding above stated preferred embodiment modes per se, where $R^1$ and $R^2$ together denote a 5 to 8 link ring possibly containing a sulfur hetero-atom or a carbonyl group and further possibly substituted with one to two $C_1$–$C_4$ alkyl group, and where $R^3$, $R^4$ and $R^5$ assume the above meanings but with A being a straight-chain or a branched $C_3$–$C_8$ alkylene group which may be interrupted by an oxygen atom or a carbonyl group, or denoting a straight-chain or a branched $C_3$–$C_8$ alkenyl group, or where $R^1$ through $R^5$ assume the meanings stated in claim 4.

Synthesis of the compounds of formula I where $R^1$ and $R^2$ together form a 5 to 8 link ring, takes place in a first step described by the equation (1) below:

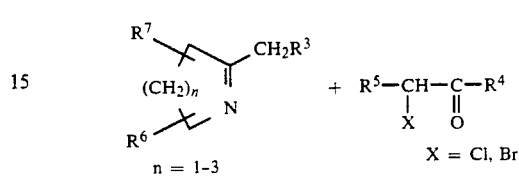

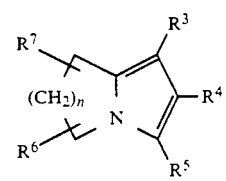

This synthesizing step is elucidated together with the following ones by means of the illustrative diphenyl-substituted pyrrolizine compounds. The first reaction stage is explained in further detail below:

Reaction diagram (1)

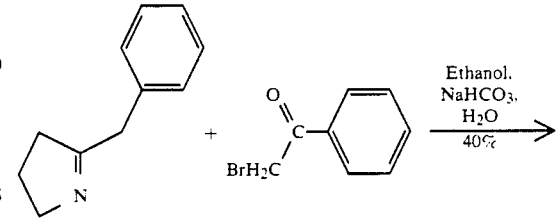

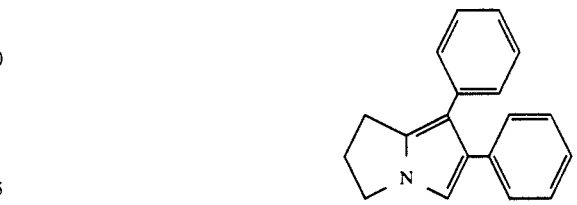

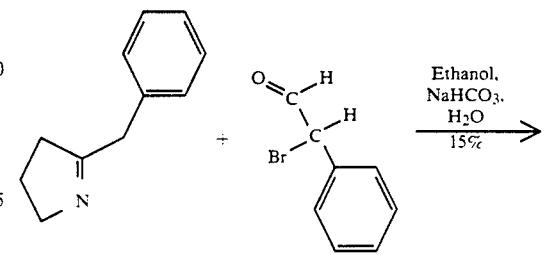

Reaction diagram (1)
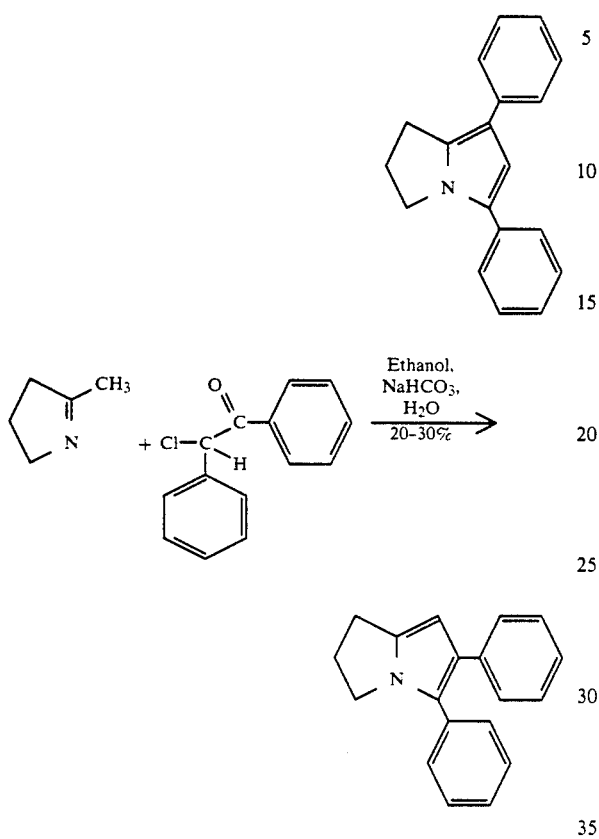
The conditions of reaction are known and described in CHEMIKER-ZEITUNG, 110, (1968) #7/8, pp 267, 271 and in ARCH. PHARM. 321, pp 159-162 (1988).
In a second stage, the formyl or methylol group is introduced into the pyrrole ring and further reaction takes place into the corresponding derivatives of acetic acid and ethanol rep. as given by the reaction diagram (2) below:
Reaction diagram (2)
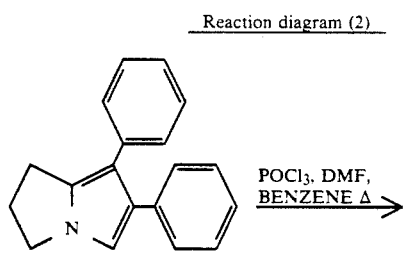
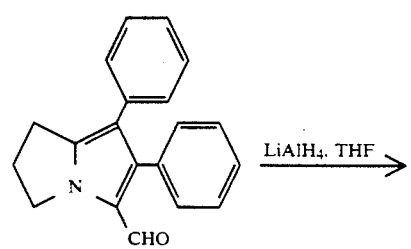
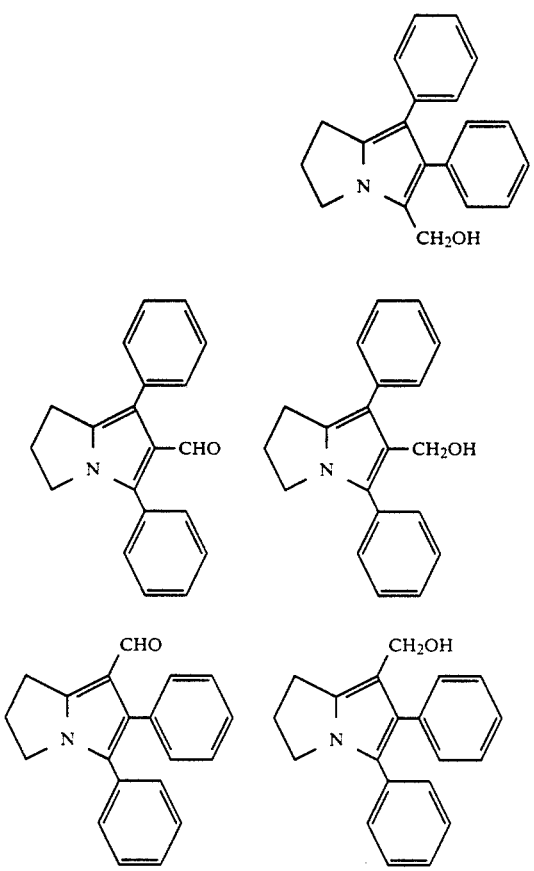
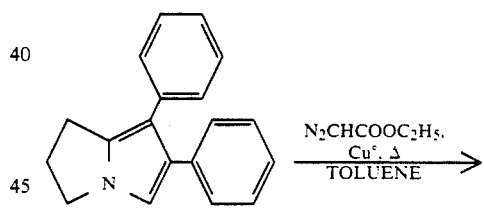
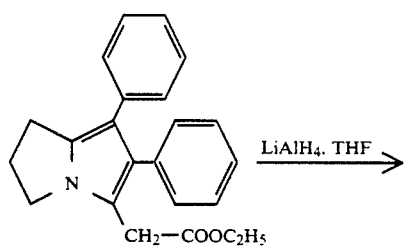
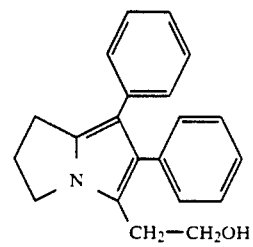

-continued
Reaction diagram (2)

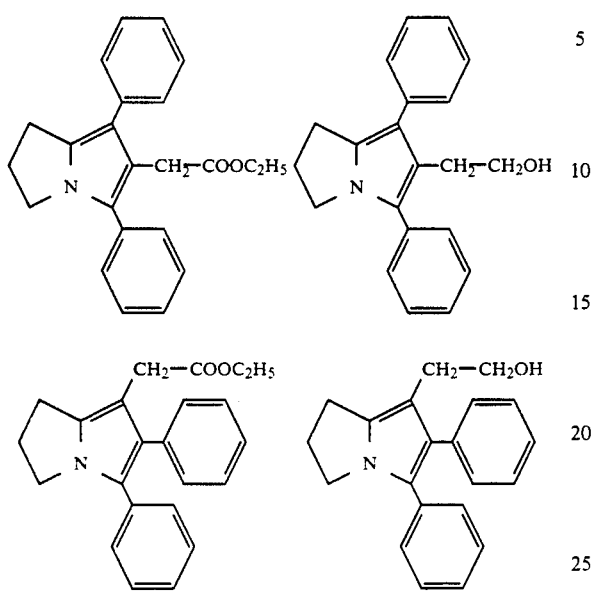

Reaction diagram (3)

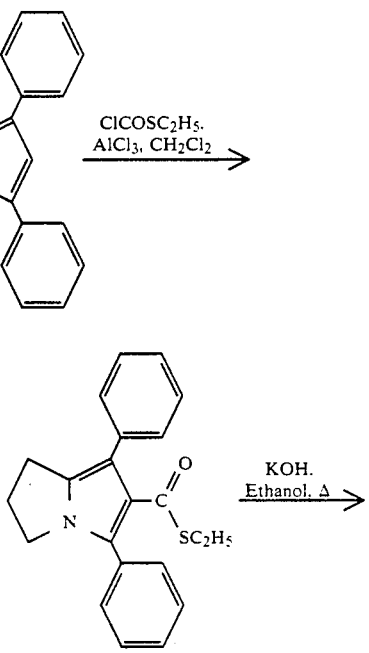

These reactions and their conditions are known and are described in CHEMIKER-ZEITUNG 110 (1968), #7/8, pp 267–271 and in ARCH. PHARM. 321, pp 159–162 (1988).

The preparation of the corresponding derivatives of formic acid, propionic acid and acrylic acid is described in ARCH. PHARM. 321, pp 545–549. It takes place according to the reaction diagrams (3) and (4).

The preparation of the corresponding butyric-acid derivatives takes place according to the reaction diagram (5). First, using the Friedels-Crafts acylation with succinic acid anhydride (E. Berlina, ORG. REAKT. 1949, 5, pp 229–289), the 4-oxobutyric acids are prepared which then are reduced by means of the Huang-Minlon variation of the Wolff-Kishner reduction with hydrazine/KOH in deithyleneglycol. The conditions of reaction are known to the expert.

The derivatives of valeric acid can be prepared by means of the 5-oxovaleric acids which in turn can be made from the pyrrolizine base bodies by the Friedel-Crafts acylation with glutaric acid anhydride in a manner similar to the preparation of the butyric acid derivatives. In similar manner the caproic acid derivatives are obtained by the Friedel-Crafts acylation of diphenyl-pyrrolizine with methyl-5-(chloroformyl-valerate/AlCl$_3$) and saponification of the 6-oxocaproic-acid-methylester derivatives and subsequent reduction of the oxovaleric acid with hydrazine/KOH.

The preparation of compounds substituted at the phenyl group takes place similarly. The hydroxy-substituted derivatives are prepared by ether splitting with BBr$_3$ from the corresponding alkoxy derivatives (TETRAHEDRON, 1968, 24, pp 2289–2292).

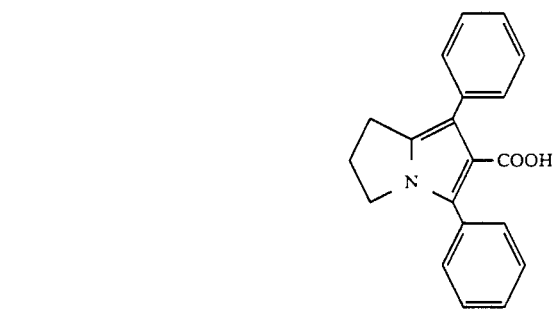

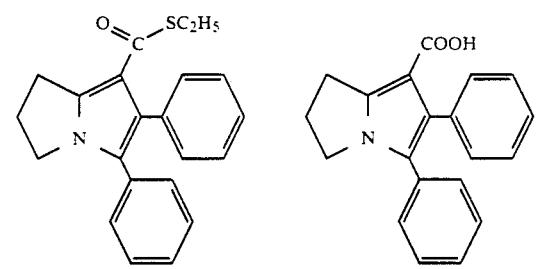

Reaction diagram (4)

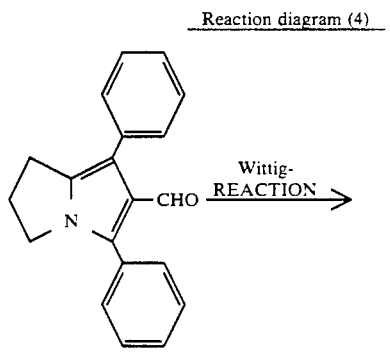

-continued
Reaction diagram (4)

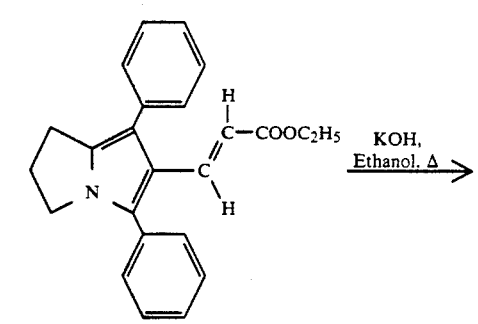

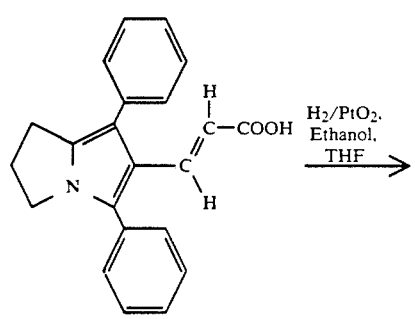

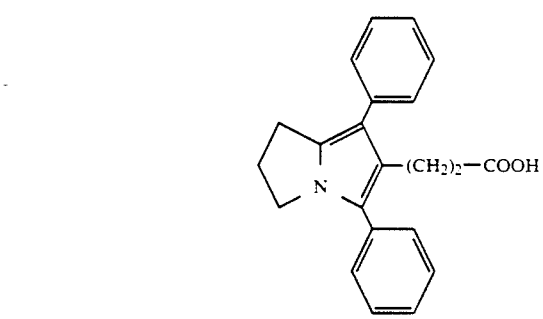

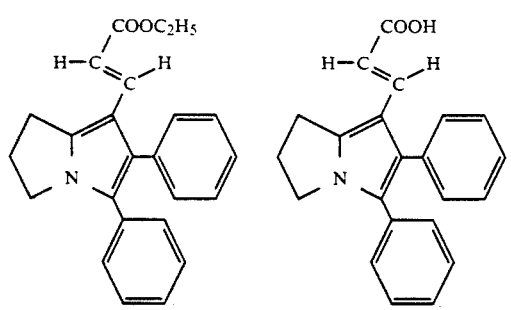

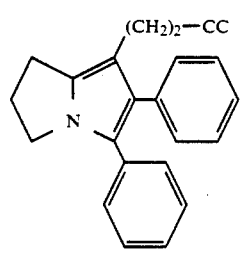

reaction diagram (5)

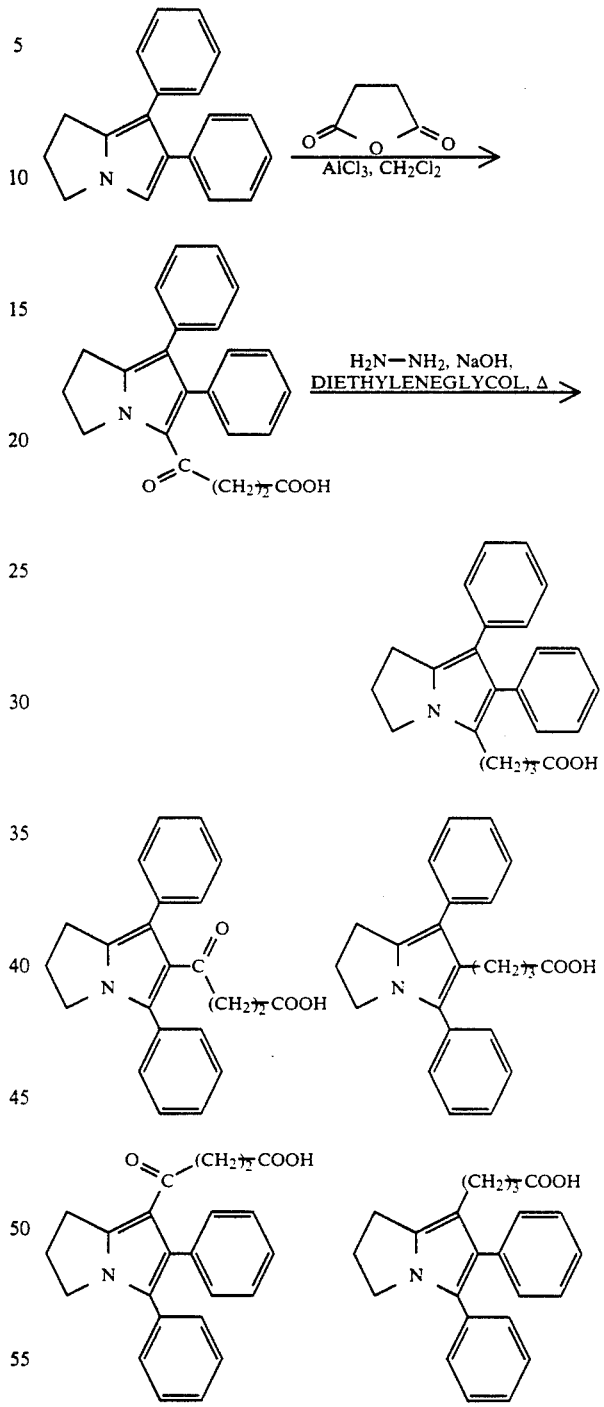

The preparation of the compounds of formula I is described below, wherein $R^1$ and $R^2$ denote a $C_1$-$C_{12}$ alkyl group. The initial material for the synthesis of these compounds are the corresponding 2,3,4- and 2,3,5-substituted pyrrole compounds of which the production is described in AUST. J. CHEM. 1966, 19, pp 1971-1885. The further synthesizing steps are elucidated illustratively below starting with 2-methyl-2,3-diphenylpyrrole and 5-methyl-2,3-diphenylpyrrole. These reactions are shown in the diagrams (6) and (7).

The first step is an alkylation of the pyrrole nitrogen atom. This reaction is carried out in conventional manner, for instance using the corresponding alkyl halides in the presence of a base, for instance alkali-metal alcoholates such as sodium methylate, sodium ethylate or potassium-t-butylate, in an inert solvent such as DMSO, ethyleneglycol methylether and the like. The alkylation also can be carried out heterogeneously with the corresponding toluene sulfonic-acid alkylesters or alkyl halides using phase transfer catalysts, in conventional manner (see for instance CAN. J. CHEM. 1977, 55, pp 4112-4116). The introduction of acid lateral chains then takes place similarly to the synthesises of the corresponding pyrrolizinyl carboxylic acids as described above.

The compounds of the invention are potent inhibitors of cyclo-oxygenase and/or lipoxygenase. Accordingly they are useful in treating the set of rheumatic illnesses and in preventing allergically induced ailments. Therefore the compounds of the invention represent effective antiphlogistics, analgetics, antipyretics, anti-allergics and broncholytics and may be used in thrombosis prophylaxis and in the prophylaxis of anaphylactic shock and to treat skin diseases such as psoriasis, urticaria, acute and chronic exanthemas of allergic and non-allergic origins.

Reaction diagram (6)

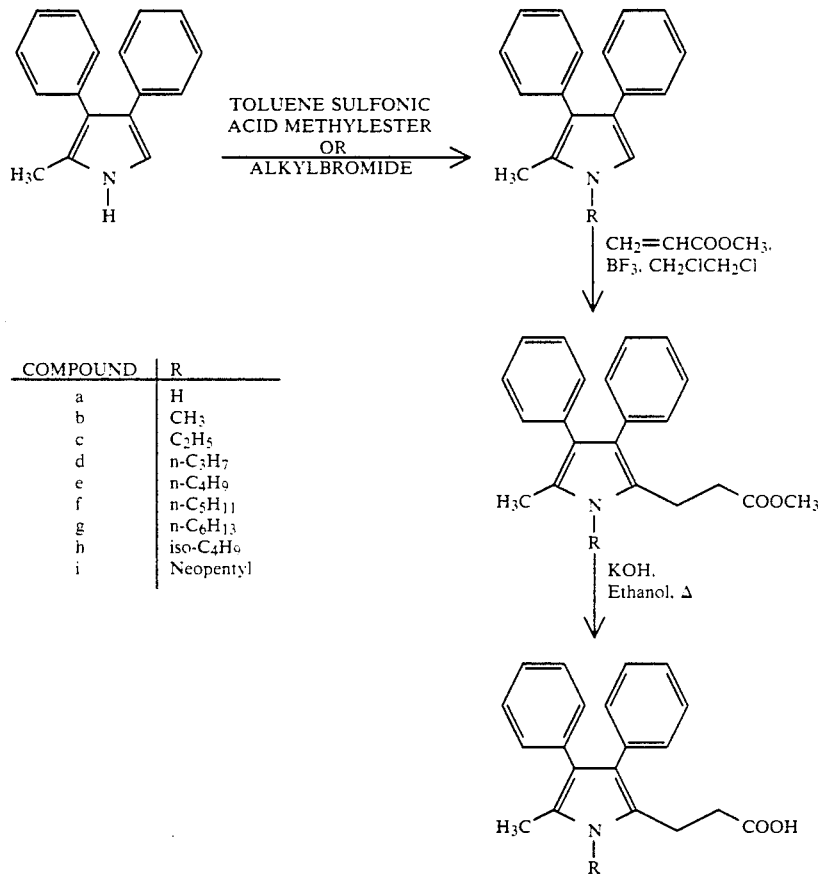

| COMPOUND | R |
|---|---|
| a | H |
| b | $CH_3$ |
| c | $C_2H_5$ |
| d | $n-C_3H_7$ |
| e | $n-C_4H_9$ |
| f | $n-C_5H_{11}$ |
| g | $n-C_6H_{13}$ |
| h | $iso-C_4H_9$ |
| i | Neopentyl |

Reaction diagram (7)

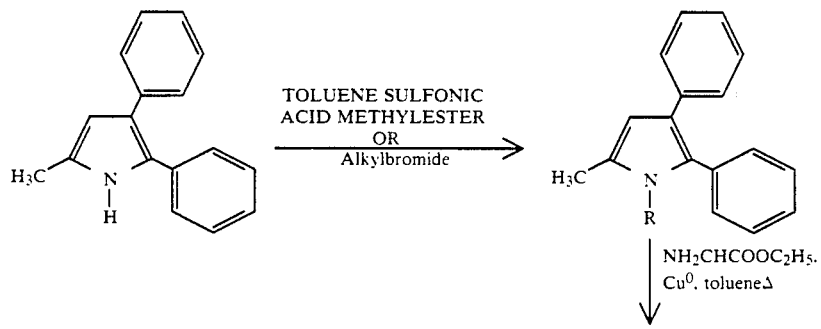

Reaction diagram (7) -continued

| COMPOUND | R |
|---|---|
| a | H |
| b | CH$_3$ |
| c | C$_2$H$_5$ |
| d | n-C$_3$H$_7$ |
| e | n-C$_4$H$_9$ |
| f | n-C$_5$H$_{11}$ |
| g | n-C$_6$H$_{13}$ |
| h | n-C$_8$H$_{17}$ |
| i | iso-C$_4$H$_9$ |
| j | Neopentyl |

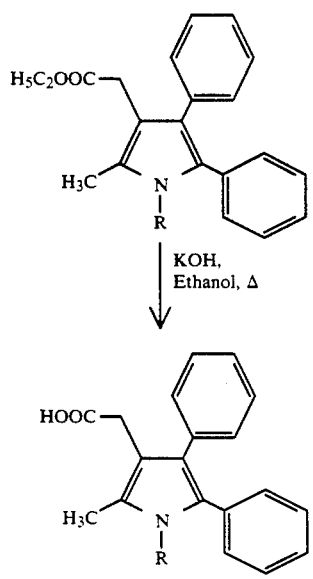

The compounds of the invention may be administered either as individual therapeutic substances or as mixtures with other active substances. They may be administered alone, but as a rule they may be administered in the form of drugs, that is as mixtures of the active substances with suitable pharmaceutical carriers or diluents. The compounds or drugs may be administered orally or parenterally but preferably they shall be dosed orally.

The kind of drug and of pharmaceutical carrier or diluent depends on the desired method of administration. Oral drugs for instance may be in the form of tablets or capsules and may contain conventional excipients such as binders (for instance syrup, acacia, gelatin, sorbite, traganth gum or polyvinylpyrrolidone), fillers (for instance lactose, sugar, maize starch, calcium phosphate, sorbite or glycine), lubricants (for instance magnesium stearate, talcum, polyethyleneglycol or silicon dioxide), disintegrates (for instance starch) or wetting agents (for instance sodium lauryl sulfate). Oral liquid preparations may be in the form of aqueous or oily suspensions, solutions, emulsions, syrups, elixirs or sprays etc. or they may be in the form of dry powders to be reconstituted with water or another suitable carrier. Such liquid preparations may contain conventional additives such as suspending agents, flavorings, diluents or emulsifiers. As regards parenteral administration, solutions or suspensions with conventional pharmaceutical carriers may be used.

The compounds or drugs of the invention can be administered to mammals (human and animal) in doses of about 0.5 mg to about 100 mg per kg of body weight per day. They can be administered in single or multiple doses.

The effectiveness of the compounds of the invention can be determined by means of the inhibition of 5-lipoxygenase or of cyclo-oxygenase. The research was carried out as follows:

TESTING TO DETERMINE THE INHIBITION OF 5-LIPOXYGENASE

The source for 5-lipoxygenase were bovine granulocytes which can form leucotrienes just as human granulocytes do. By stimulation with calcium-ionophore (see BIOCHEM. BIOPHYS. ACTA 1984, 795, pp 499–503), mainly LTC$_4$ (leucotriene C$_4$) and LTB$_4$ (leucotriene B$_4$) are formed from endogenous arachidonic acid. The isolation of the granulocytes and the implementation of the enzyme reaction are conventional (see BIOCHEM. BIOPHYS. ACTA 1984, 795 pp 499–503). The blood protected against clotting by EDTA first is centrifuged for that purposed and the thrombotic excess is removed. Following lysis of the erythrocytes with water the lymphocytes and monocytes are separated from the granulocytes by means of a Ficoll gradient. The granulocytes are set to a specific cell number. The enzyme reaction is then begun in the presence or absence of the test substances following the addition of Ca$^{2+}$ with calcium ionophore. The synthesis of the leucotrienes is stopped after 5 minutes by adding a mixture of methanol and acetonitrile containing PGB2 as the internal standard and NDGA as the anti-oxidant. Next the samples are diluted in water and processed in the manner described in J. CHROMATOGR. 1896, 378, pp 208–214. LTB$_4$ is measured at the absorption maximum at 270 nm. The arachidonic acid metabolites are observed present in this research in approximately quantitative manner.

TESTING TO DETERMINE THE INHIBITION OF CYCLO-OXYGENASE

In this test the 12-HHT amount of 12-hydroxyheptadecatriene acid or prostaglandin E$_2$ amount formed by bovine thrombocytes following addition of calcium ionophore is determined by uv detection following HPLC separation. Following centrifuging of the bovine blood, the thrombocytes are isolated from the surnatant. The enzyme reaction and the isolation of the formed metabolites take place as when determining the 5-lipoxygenase inhibition, however the incubation time was one minute. The detection of 12 HHT following HPLC separation takes place at 232 nm.

Tables 1 and 2 list the test results for the compounds of the invention, The test substances were at concentrations of 10 μM.

The Examples below illustrate the invention. All temperatures are uncorrected. The ir spectra—unless noted otherwise—are from KBr molded articles. The NMR spectra, unless noted otherwise, are 90 Mhz spectra, recorded in $CDCl_3$ with tetramethylsilane (TMS) as the internal standard.

The preparation and the properties of the compounds used as initial materials used in part for the reactions below and listed in Tables 3, 4 and 5 are described in the following literature:
ARCH. PHARM. 312, pp 896-907 (1979)
ARCH. PHARM. 319, pp 500-505 (1986)
ARCH. PHARM. 321, pp 159-162 (1988)
ARCH. PHARM. 321, pp 545-549 (1988)
CHEMIKER ZEITUNG, 110, (1986), 7/8, pp 267-271.

TABLE 2

INHIBITION OF 5-LIPOXYGENASE BY 2-METHYL-DIPHENYLPYRROLE-ACETIC-ACIDS

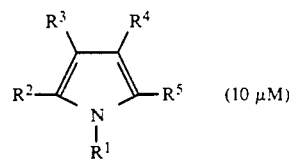

(10 μM)

| $R^1$ | $R^2$ | $R^3$ | $R^4$ | $R^5$ | INHIBITION (%) (Lipoxygenase) |
|---|---|---|---|---|---|
| n-$C_4H_9$ | $CH_3$ | Phenyl | Phenyl | $(CH_2)_2CO_2H$ | 94 |
| n-$C_5H_{11}$ | $CH_3$ | Phenyl | Phenyl | $(CH_2)_2CO_2H$ | 99 |
| n-$C_6H_{13}$ | $CH_3$ | Phenyl | Phenyl | $(CH_2)_2CO_2H$ | 99 |
| Neo-pentyl | $CH_3$ | Phenyl | Phenyl | $(CH_2)_2CO_2H$ | 97 |

TABLE 1

INHIBITION OF 5-LIPOXYGENASE AND OF CYCLO-OXYGENASE BY PYRROLIZINE COMPOUNDS.

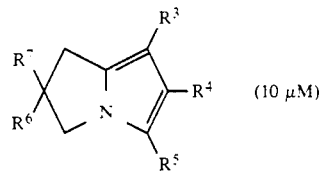

(10 μM)

| COMPOUND Nr. | $R^3$ | $R^4$ | $R^5$ | $R^6$ | $R^7$ | INHIBITION % Lipoxygenase | Cyclooxygenase |
|---|---|---|---|---|---|---|---|
| | Phenyl | $(CH_2)_4CO_2H$ | Phenyl | H | H | 82 | |
| | Phenyl | $(CH_2)_5CO_2H$ | Phenyl | H | H | 80 | |
| | $(CH_2)_4CO_2H$ | Phenyl | Phenyl | H | H | 86 | |
| | $(CH_2)_5CO_2H$ | Phenyl | Phenyl | H | H | 86 | |
| | Phenyl | Phenyl | $CH_2CO_2H$ | $CH_3$ | $CH_3$ | 94 | 99 |
| | Phenyl | Phenyl | $(CH_2)_2CO_2H$ | $CH_3$ | $CH_3$ | 91 | 97 |
| | $(CH_2)_2CO_2H$ | Phenyl | Phenyl | $CH_3$ | $CH_3$ | 93 | |
| | $(CH_2)_5CO_2H$ | Phenyl | Phenyl | $CH_3$ | $CH_3$ | 96 | |
| | Phenyl | Phenyl | $CH_2CO_2H$ | H | H | | 91 |
| | Phenyl | Phenyl | $CH=CH-CO_2H$ | H | H | 80 | |
| | $CH=CHCO_2H$ | Phenyl | Phenyl | $CH_3$ | $CH_3$ | 91 | |
| | Phenyl | $C_6H_{13}$ | $CH=CHCO_2H$ | H | H | 82 | |
| | Phenyl | m-Chlorphenyl | $(CH_2)_2CO_2H$ | H | H | 89 | |
| | Phenyl | p-Chlorphenyl | $(CH_2)_2CO_2H$ | H | H | 98 | |
| | Phenyl | p-Tolyl | $(CH_2)_2CO_2H$ | H | H | 92 | |
| | Phenyl | p-Methoxyphenyl | $(CH_2)_2CO_2H$ | H | H | 91 | |
| | Phenyl | p-Phenoxyphenyl | $(CH_2)_2CO_2H$ | H | H | 98 | 70 |
| | Phenyl | α-naphthyl | $(CH_2)_2CO_2H$ | H | H | 94 | |
| | Phenyl | p-Fluorphenyl | $(CH_2)_2CO_2H$ | $CH_3$ | $CH_3$ | | 93 (3.3 μM) |
| | Phenyl | p-Tolyl | $(CH_2)_2CO_2H$ | $CH_3$ | $CH_3$ | | 93 (3.3 μM) |
| | Phenyl | p-Phenoxyphenyl | $(CH_2)_2CO_2H$ | $CH_3$ | $CH_3$ | 98 (3.3 μM) | |

TABLE 3

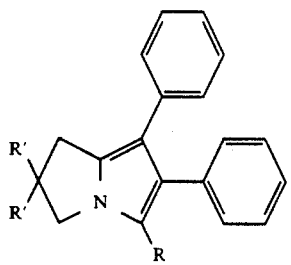

| EXAMPLE Nr. | R | R' = H | R' = CH₃ |
|---|---|---|---|
| 1 | H | 1a | 1b |
| 2 | CHO | 6a | 6b |
| 3 | CH₂OH | 9a | 9b |
| 4 | CH₂COOC₂H₅ | 12a | 12b |
| 5 | (CH₂)₂OH | 15a | 15b |
| 6 | COOH | 18a | 18b |
| 7 | CH₂COOH | 23a | 23b |
| 8 | (CH₂)₂COOCH₃ | 26a | 26b |
| 9 | (CH₂)₂COOH | 27a | 27b |
| 10 | CH=CHCOOC₂H₅ (E) | 30 | |
| 11 | CH=CHCOOH (E) | 33 | |

TABLE 4

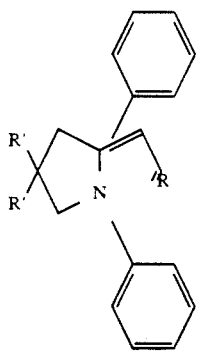

| EXAMPLE Nr. | R | R' = H | R' = CH₃ |
|---|---|---|---|
| 12 | H | 2a | 2b |
| 13 | CHO | 7a | 7b |
| 14 | CH₂OH | 10a | 10b |
| 15 | CH₂COOC₂H₅ | 13a | 13b |
| 16 | (CH₂)₂OH | 16a | 16b |
| 17 | COSC₂H₅ | 19a | 19b |
| 18 | COOH | 21a | 21b |
| 19 | CH₂COOH | 24a | 24b |
| 20 | CH=CHCOOC₂H₅ (E) | 28 | |
| 21 | CH=CHCOOH (E) | 30 | |
| 22 | (CH₂)₂COOH | 32 | |

TABLE 5

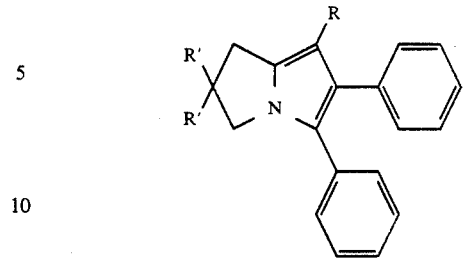

| EXAMPLE Nr. | R | R' = H | R' = CH₃ |
|---|---|---|---|
| 23 | H | 3a | 3b |
| 24 | CHO | 8a | 8b |
| 25 | CH₂OH | 11a | 11b |
| 26 | CH₂COOC₂H₅ | 14a | 14b |
| 27 | (CH₂)₂OH | 17a | 17b |
| 28 | COSC₂H₅ | 20a | 20b |
| 29 | COOH | 22a | 22b |
| 30 | CH₂COOH | 25a | 25b |
| 31 | CH=CHCOOC₂H₅ (E) | 29a | 29b |
| 32 | CH=CHCOOC₂H₅ (Z) | | 29b' |
| 33 | CH=CHCOOH (E) | 31a | 31b |
| 34 | CH=CHCOOH (Z) | | 31b' |
| 35 | (CH₂)₂COOH | 33a | 33b |

GENERAL PROCEDURE FOR PREPARING THE 4-(DIPHENYL-2,3-DIHYDRO-1H-PYRROLIZINYL)-4-OXOBUTYRIC ACIDS

With ice cooling and stirring, 8.8 mmoles (1.17 g) of AlCl₃ are added in batches over five minutes to a solution of 4 mmoles of diphenyl-2,3-dihydro-1H-pyrrolizine and 4 mm (0.40 g) of succinic acid anhydride. Then agitation continues for 45 minutes at room temperature. Thereupon the batch is poured into 150 ml ice water. After adding 4 ml of 8% H₃PO₄, extraction is performed three times with CHCl₃, the organic phases are dried with Na₂SO₄ and the solvent is distilled. Product isolation is by means of column chromatography (silica gel, 1st ether, 2nd ether/THF 1+1). The product fractions are concentrated, the residue is dissolved in a little CHCl₃. After adding n-hexane and new concentration, the product is precipitated.

GENERAL PROCEDURE FOR PREPARING THE 4-(DIPHENYL-2,3-DIHYDRO-1H-PYRROLIZINYL)-BUTYRIC ACIDS 0.5 mmoles of 4-(diphenyl-2,3-dihydro-1H-pyrrolizinyl)-4-oxobutyric acid are mixed with 10 ml of diethyleneglycol, 50 mmoles (2.8 g) of KOH and 30 mmoles (1.5 g) of hydrazine hydrate. The batch is heated 1 hour till reflux (bath temperature 170° C.). Next the reflux condenser is replaced by a distillation bridge and the temperature is raised until the inside is at about 210° C. This temperature is then maintained for 2 h. Following cooling, the batch is poured into 150 ml H₂O, acidified with 8% H₃PO₄ and extraction is carried out three times with ether. The extracts are washed with H₂O, dried and concentrated. The product is isolated with column chromatography (silica gel, ether/THF 4+1 in 39, diisopropylether in 40, ether in 41a and ether/n-hexane 4+1 in 41b) and is precipitated using n-hexane.

GENERAL PROCEDURE FOR PREPARING THE 5-(DIPHENYL-2,3-DIHYDRO-1H-PYRROLIZINYL)-5-OXOVALERIC ACIDS 4 mmoles of diphenyl-2,3-dihydro-1H-pyrrolizine are reacted in 16 ml of absolute $CH_2Cl_2$ with 4 mmoles (0.46 g) of glutaric acid anhydride and 8.8 mmoles (1.17 g) of $AlCl_3$ similarly to the procedure for making the 4-(diphenyl-2,3-dihydro-1H-pyrrolizinyl)-4-oxobutyric acid ("s.S." 222). In deviation, the batch is poured into ice water immediately after the addition of $AlCl_3$ and then is processed further. Product purification takes place by column chromatography (silica gel/ether).

GENERAL PROCEDURE FOR PREPARING THE 5-(DIPHENYL-2,3-DIHYDRO-1H-PYRROLIZINYL)-5-VALERIC ACIDS 0.5 mmoles of 5-(diphenyl-2,3-dihydro-1H-pyrrolizinyl)-5-oxovaleric acids are reacted similarly to the procedure for making the 4-(diphenyl-2,3-dihydro-1H-pyrrolizinyl)-4-oxobutyric acids. The produce is isolated by column chromatography (silica gel, ether) and precipitated by means of n-hexane.

GENERAL PROCEDURE FOR PREPARING THE 6-(DIPHENYL-2,3-DIHYDRO-1H-PYRROLIZINYL)-6-OXOCAPROIC-ACID METHYLESTERS

With ice cooling and while stirring, 22 mmoles (2.93 g) of $AlCl_3$ are added over 5 minutes and in batches to the solution of 10 mmoles of diphenyl-2,3-dihydro-1H-pyrrolizine and 10 mmoles (1.79 g) of methyl-5-(chloroformyl)-valerate in 50 ml of absolute $CH_2Cl_2$. Immediately thereafter the batch is poured into 150 ml of ice-cooled 10% NaCl solution. Upon addition of 4 ml of 8% $H_3PO_4$, extraction with ether is carried out three times, the organic phases are dried with $Na_2SO_4$ and the solvent is distilled. The product is isolated by means of column chromatography (silica gel, 1st n-hexane/ether 3+2, 2nd n-hexane/ether 1+4 in 48, 50a and 50b, or 1st toluene, 2nd hexane/ether 1+4 in 49). First the eluates are concentrated to about 100 ml, then they are washed twice with 0.05 n NaOH and twice with 10% NaCl solution and lastly they are dried with $Na_2SO_4$. When the solution is concentrated the products precipitate or, following distillation of the solvent, crystallize.

GENERAL PROCEDURE FOR PREPARING THE 6-(DIPHENYL-2,3-DIHYDRO-1H-PYRROLIZINYL)-6-CAPROIC ACIDS

The solution of 1 mmole of 6-(diphenyl-2,3-dihydro-1H-pyrrolizinyl)-6-oxocaproic-acid methylester in 10 ml of ethanol is heated to boiling. 5 ml of 10% KOH previous degassed by boiling are dripped into that solution and heating continues another 15 minutes with reflux. Following cooling the batch is poured into 100 ml of 5% NaCl and then is acidified with 8% $H_3PO_4$ and extraction is carried out three times with ether. The organic phases are dried by means of $Na_2SO_4$ and concentrated. The residue is reacted with 50 mmoles (2.8 g) of KOH and 30 mmoles (1.5 g) of hydrazine hydrate in 10 ml of diethylene glycol similarly to the preparation procedure for the 4-(diphenyl-2,3-dihydro-1H-pyrrolizinyl)-butyric acids and is purified by column chromatography with silica gel.

The compounds so prepared and several physical properties of theirs are listed in the Tables 6 through 8 below.

GENERAL PROCEDURE FOR PREPARING THE 2-(DIPHENYL-2,3-DIHYDRO-1H-PYRROLIZINYL)-PROPIONIC-ACID ETHYLESTERS 5 mmoles of diphenyl-2,3-dihydro-1H-pyrrolizine dissolved in 4 ml of absolute toluene are reacted with 7.5 mmoles (0.96 g) of 2-diazopropionic-acid ethylester dissolved in 2 ml of absolute toluene similarly to the procedure for preparing the diphenyl-2,3-dihydro-1H-pyrrolinyl acetic-acid ethylesters. However the time of reaction is 2 h. Purification is column chromatography ($Al_2O_3$, n-hexane/ether 9+1). The products are precipiated with ethanol.

GENERAL PROCEDURE FOR SAPONIFYING THE 2-(DIPHENYL-2,3-DIHYDRO-1H-PYRROLIZINYL) PROPIONIC-ACID ETHYLESTERS 5 mmoles of 54 or 0.5 mmoles of 55a and 55b, dissolved in 12 ml or 9 ml resp. of ethanol are reacted with 8 ml or 2.5 ml resp. of 10% aqueous KOH similarly to the procedure for saponifying the diphenyl-2,3-dihydro-1H-pyrrolizinyl-acetic-acid ethylesters. The time of saponification is 15 min in 54, 60 min in 55a, and 55b. Purification is by column chromatography (silica gel, 1st n-hexane/ether 1+1, 2nd ether). After the eluates have been concentrated, the products are precipitated with n-hexane.

The compounds so prepared together with some of their properties are listed in Table 6 and the Table 9.

TABLE 6

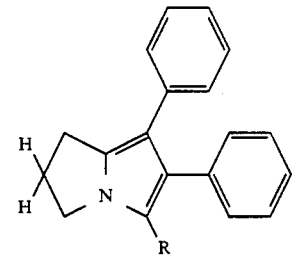

| EXAMPLE Nr. | R | | MELTING POINT °C. | IR[1] |
|---|---|---|---|---|
| 36 | CO(CH$_2$)$_2$COOH | 36 | 187-188 | 1710, 1635 |
| 37 | (CH$_2$)$_3$COOH | 39 | 166-167 | 1705 |
| 38 | CO(CH$_2$)$_3$COOH | 42 | 142-143 | 1710, 1635 |
| 39 | (CH$_2$)$_4$COOH | 45 | 146 | 1710 |
| 40 | CO(CH$_2$)$_4$COOH | 48 | 99 | 1740, 1630 |
| 41 | (CH$_2$)$_5$COOH | 51 | — | * |
| 42 | CH(CH$_3$)COOC$_2$H$_5$ | 54 | — | 1730 |
| 43 | CH(CH$_3$)COOH | 56 | 173 | 1705 |

[1](C=O) Band
*$^1$H-NMR. δ(ppm) = 1.06-1.78(m, 6H, —(CH$_2$)$_3$—CH$_2$—CO—), 2.10-2.40(m, 2H, —CH$_2$—CO—), 2.40-2.7o(m, 4H, Pyr—CH$_2$ and C-2), 3.02(t, 2H, J=7Hz, C-1), 3.94(t, 2H, J=7Hz, C-3), 6.97-7.31(m, 10H, Arom.)

TABLE 7

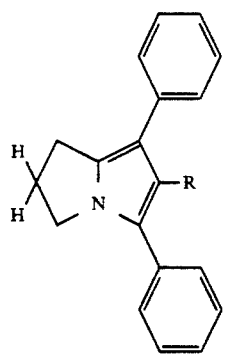

| EXAMPLE Nr. | R | MELTING POINT °C | IR[1] |
|---|---|---|---|
| 44 | CO(CH₂)₂COOH | 37 231–234 | 1715, 1680 |
| 45 | (CH₂)₃COOH | 40 176–178 | 1715 |
| 46 | CO(CH₂)₃COOH | 43 128 | 1710, 1660 |
| 47 | (CH₂)₄COOH | 46 126–127 | 1700 |
| 48 | CO(CH₂)₄COOCH₃ | 49 112 | 1745, 165β |
| 49 | (CH₂)₅COOH | 52 63 | 1710 |

[1] (C=O) Band

TABLE 8

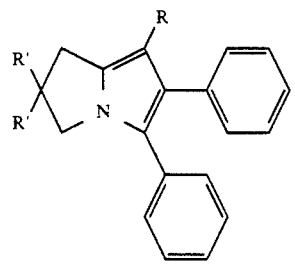

| EXAMPLE Nr. | R | R' = H | a | b | MELTING PT. °C a | b | IR[1] a | b |
|---|---|---|---|---|---|---|---|---|
| 50 | CO(CH₂)₂COOH |  | 38a | 38b | 190–191 | 187–188 | 1715, 1665, 1645 | 1715, 1645 |
| 51 | (CH₂)₃COOH |  | 41a | 41b | 146–148 | 192–194 | 1705 | 1710 |
| 52 | CO(CH₂)₃COOH |  | 44a | 44b | 109 | 167 | 1720, 1660 | 1715, 1660 |
| 53 | (CH₂)₄COOH |  | 47a | 47b | 111–112 | 1705 | 129–130 | 1715 |
| 54 | CO(CH₂)₄COOCH₃ |  | 50a | 50b | 92 | 1735, 1645 |  | 1740, 1655 |
| 55 | (CH₂)₅COOH |  | 53a | 53b | 123 | 1710 | 122 | 1710 |

[1] (C=O) Band

TABLE 9

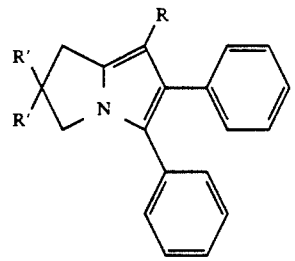

| EXAMPLE Nr. | R | R' = H | CH₃ | MELTING PT. a | b | IR (C=O) a | b |
|---|---|---|---|---|---|---|---|
| 56 | CH(CH₃)COOC₂H₅ | 55a | 55b | 133 | 136 | 1730 | 1740 |
| 57 | CH(CH₃)COOH | 57a | 57b | 190 | 1705 | 226 | 1710 |

EXAMPLE 58

5-(1-(DIPHENYL-2,3-DIHYDRO-1H-PYRROLI-ZINE-7-YL)-ETHYL)-2,3-DIMETHYL-1,3-DIOXAN-4,6-DIONE (59a)

The solution of 4 mmoles (1.04 g) of 3a, 4 mmoles (0.58 g) of 2,2-dimethyl-1,3-dioxan-4,6-dione (Meldrum's acid) and 8 mmoles (0.35 g) of freshly distilled acetaldehyde in 40 ml of acetonitrile is made to stand for 24 h at 30° C. Following cooling in the ice bath, the precipitated product is evacuated.

Yield: 0.44 g (26%).

melting point: 169° C. (with dissociation).

IR: $\nu_{max}$=1790 (C=O), 1605 (C=C)/cm.

EXAMPLE 59

5-(1-(2,3-DIMETHYL-5,6-DIPHENYL-2,3-DIHYDRO-1H-PYRROLIZINE-7-YL)ETHYL)-2,2-DIMETHYL-1,3-DIOXAN-4,6-DIONE (59b)

4 mmoles (1.15 g) of 3b are reacted in the manner described in relation to 59a with acetaldehyde and Meldrum's acid.

Yield: 1.35 g (74%).

Ir: $\nu_{max}$=1790 (C=O), 1755 (C=O), 1605 (C=C)/cm.

EXAMPLE 60

3-(5,6-DIPHENYL-2,3-DIHYDRO-1H-PYRROLIZINE-7-YL) BUTYRIC-ACID ETHYLESTERS (60a)

1 mmole of 59a is dissolved in a mixture of 5 ml of absolute pyridine and 1.0 ml of absolute ethanol. After adding some copper powder, the batch is heated to reflux for 3 h. The copper power is evacuated and the solvent is distilled in vacuum. The product is isolated from the residue by column chromatography (silica gel, n-hexane/$CH_2Cl_2$ 1+2).

Yield: 96.5 mg (25%).

IR: $\nu_{max}$=1735 (C=O), 1605 (C=C)/cm.

EXAMPLE 61

3-(2,3-DIMETHYL-5,6-DIPHENYL-2,3-DIHYDRO-1H-PYRROLIZINE-7-YL)BUTYRIC-ACID ETHYLESTER (60b)

2.5 mmoles of 59b are dissolved in a mixture of 20 ml absolute pyridine and 2 ml of absolute ethanol and upon addition of some copper powder the batch is reacted as described for 60a. Purification is by column chromatography (silica gel, n-hexane/$CH_2Cl_2$ 2+1) in isolation.

Yield: 0.68 g (68%).

IR: $\nu_{max}$=1745 (C=O), 1605 (C=C)/cm.

EXAMPLE 62

3-(5,6-DIPHENYL-2,3-DIHYDRO-1H-PYRROLIZINE-7-YL)-BUTYRIC ACID (61a)

The eluates are concentrated. The product is made to crystallize using a little ether and then is made to precipitate extensively by adding n-hexane.

Yield: 63 mg (36%).

Melting point: 157° C. (with dissociation).

IR $\nu_{max}$=3300-2400 (OH), 1710 (C=O), 1605 (C=C)/cm.

EXAMPLE 63

3-(2,2-DIMETHYL-5,6-DIPHENYL-2,3-DIHYDRO-1H-PYRROLIZINE-7-YL) BUTYRIC-ACID (61b)

The product precipitates when the eluates are concentrated.

Yield: 0.26 g (46%).

Melting point: 202°-208° C. (with dissociation).

GENERAL PROCEDURE FOR PREPARING THE TRIMETHYLPHENYL-2,3-DIHYDRO-1-H-PYRROLIZINES 0.05 moles (5.6 g) of 2,4,4-trimethyl-Δ1pyrroline, dissolved in 25 ml of absolute ethanol, are reacted with 0.05 moles (10.7 g) of 1-bromo-1-phenylacetone (in 63) or α-bromo-propiophenone (in 64) in a manner analogous to the synthesis of 3a. In deviation from that reference, here, following addition of the NaHCO3 solution (0.06 moles in 40 ml of $H_2O$) are heated only 4 h to reflux. Purification is carried out by means of column chromatography ($Al_2O_3$, n-hexane/ether 9+1). Oil remains following concentration of the eluate.

GENERAL PROCEDURE FOR PREPARING THE TRIMETHYLPHENYL-2,3-DIHYDRO-1H-PYRROLIZINYL-ACETIC-ACID ETHYLESTERS 5 mmoles (1.13 g) of 63 or of 64, dissolved in 5 ml of absolute toluene, are reacted with 7.5 mmoles (0.86 g) of diazo-acetic-acid ethylester dissolved in 4 ml of absolute toluene similarly to the procedure for preparing the diphenyl-1,2,3-dihydro-1H-pyrrolizinyl acetic-acid ethylesters. The products are obtained as oils following column chromatography ($Al_2O_3$, 1st n-hexane/ether 9+1, 2nd n-hexane/ether 3+2).

SAPONIFICATION OF THE TRIMETHYLPHENYL-2,3-DIHYDRO-1H-PYRROZINYL-ACETIC-ACID ETHYLESTERS 1.5 mmoles of 65 or 0.5 mmoles of 66, dissolved in 4 ml or 12 ml resp. of ethanol are reacted with 2.5 ml or 7.5 ml resp. of 10% aqueous KOH similarly to the procedure for saponifying the diphenyl-2,3-dihydro-1H-pyrrolinyl-acetic-acid ethylesters. Purification is by column chromatography.

The compounds and several of their properties are listed in the Tables 10 and 11 below.

TABLE 10

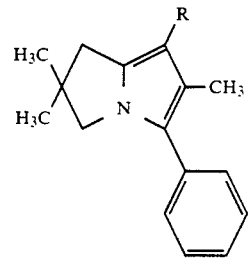

| EXAMPLE Nr. | R | MELTING PT. | IR[1] |
|---|---|---|---|
| 64 | H | 63 | — | 1605 |
| 65 | $CH_2COOC_2H_5$ | 65 | — | 1735 |
| 66 | $CH_2COOH$ | 67 | 168 | 1715 |

TABLE 11

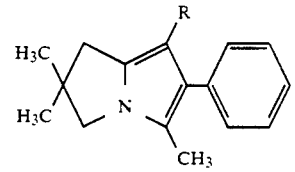

| R | | MELTING PT. | IR[1] |
|---|---|---|---|
| 67 | H | 64 | 58-60 | 1595 (C=C) |
| 68 | $CH_2COOC_2H_5$ | 66 | | 1740 |
| 69 | $CH_2COOH$ | 68 | 141 | 1710 |

[1](C=O) band, unless stated otherwise

EXAMPLE 70

5-(n-HEXYL)-7-PHENYL-2,3-DIHYDRO-1H-PYRROLIZINE (69)

In order to dissolve 35 mmoles of n-octanal in 15 ml of ether and 5 ml of dioxan, a solution of 35 mmoles (5.6 g) of bromine in 5 ml of $CH_2Cl_2$ is slowly added while stirring. This batch then is mixed with 50 ml ether and to neutralize HBr, the mixture is washed carefully twice with a 5% NaHCO3 solution. The organic phase is dried by means of $Na_2SO_4$ and concentrated. The residue is dissolved in 50 ml ethanol and added to a mixture of 30 mmoles of 2 benzyl-Δ1-pyrroline[99], 50 ml of ethanol and 50 ml of 10% NaHCO3 solution. After stirring for 24 at room temperature, the batch is poured into 500 ml of 10% NaCl and extraction is carried out twice with ether. The organic phases are dried by means Na$_2$SO$_4$, the solvent is distilled and the pyrrolizines so obtained, 69 and 70, are isolated by column chromatography (Al$_2$O$_3$, n-hexane/ether 9+1).

The two isomeric pyrrolizines then are dissolved in 50 ml of dichloroethane and are mixed a total of four times, 15 minutes apart, each time with 17 mmoles of acrylic-acid methylester and 1.0 ml of BF$_3$ etherate. Following addition of 200 ml of 5% NaCl solution, the batch is extracted twice with ether. Following drying by means of Na$_2$SO$_4$, The solvent is distilled and the unconverted 69 is isolated by means of column chromatography (Al$_2$O$_3$, n-hexane/ether 9+1). The eluates are concentrated. The remaining oil solidifies after some time.

Yield: 1.23 g (16%).
Melting point: 46°-47° C.
C$_{19}$H$_{25}$N (224.1).
IR: $\nu_{max}$=1610 (C=C)/cm.
$^1$H-NMR: δ(ppm)=0.73-1.06 (m, 3 H, —CH$_3$), 1.06-1.76 (m, 8 H, —CH$_2$—), 2.33-2.72 (m, 4 H, C-2 und Pyr—CH$_2$—), 3.04 (t, 2 H, J=7 Hz, C-1), 3.83 (t, 2 H, J=7 Hz, C-3), 6.20 (s, 1 H, C-5), 6.95-7.56 (m, 5 H, Arom.)

EXAMPLE 71

5-(5-(n-HEXYL)-7-PHENYL-2,3-DIHYDRO-1H-PYRROLIZINE-6YL)-5-OXOVALERIC ACID (71)

5 mmoles of 5-(n-hexyl)-7-phenyl-2,3-dihydro-1H-pyrrolizine 69 are reacted in 20 ml of CH$_2$Cl$_2$ with 5 mmoles (0.5 g) of glutaric acid anhydride and 11 mmoles (1.47 g) of AlCL$_3$ similarly to the procedure for preparing the 5-(diphenyl-2,3-dihydro-1H-pyrrolizinyl)-5-oxovaleric-acids. The product is purified by column chromatography (silica gel, 1st n-hexane/ether 1+1, 2nd ether). After the eluates are concentrated, 71 remains as an oil.

Yield 0.40 g (21%).
C$_{24}$H$_{31}$NO$_3$ (381.5).
$^1$H-NMR: δ(ppm)32 0.69-1.07 (m, 3 H, —CH$_3$), 1.07-1.98 (m, 10 H, —CH$_2$—), 1.98-2.65 (m, 6 H, C-2 und —CO—CH$_2$—CH$_2$CH$_2$—CO—), 2.65-2.95 (m, 4 H, C-1 und Pyr—CH$_2$—), 3.91 (t, 2 H, J=7 Hz, C-3), 7.07-7.47 (m, 5 H, Arom.)

EXAMPLE 72

5-(5-(n-HEXYL)-7-PHENYL-2,3-DIHYDRO-1H-PYRROLIZINE-6YL)-VALERIC ACID (72)

1 mmole of 71 is reacted in 10 ml of diethyleneglycol with 50 mmoles (2.8 g) of KOH and 30 mmoles (1.5 g) of hydrazine hydrate similarly to the procedure for reducing the 4-(diphenyl-2,3-dihydro-1H-pyrrolizinyl)-4-oxobutyric acids. Product purification is by means of column chromatography (silica gel/diisopropylether). After concentrating the eluates, 72 remains as an oil.

Yield 0.20 g (54%).
C$_{24}$H$_{33}$NO$_2$ (367.5).
IR: $\nu_{max}$=3600-2400 (OH), 1710 (C=O), 1605 (C=C) cm$^{-1}$
$^1$H-NMR: δ(ppm)=0.72-1.12 (m, 3 H, —CH$_3$), 1.12-1.78 (m, 12 H, —CH$_2$—), 2.08-2.70 (m, 8 H, C-2, —CH$_2$—CO— und 2x Pyr—CH$_2$—), 2.90 (t, 2 H, J=7 Hz, C-1), 3.87 (t, 2 H, J=7 Hz, C-3), 6.95-7.44 (m, 5 H, Arom.).

EXAMPLES 73, 74

5-(n-HEXYL)-7-PHENYL-2,3-DIHYDRO-1H-PYRROLIZINE-6-YL-CARBALDEHYDE (73) AND 6-(n-HEXYL)-7-PHENYL-2,3-DIHYDRO-1H-PYRROLIZINE-5-YL-CARBALDEHYDE (74)

35 mmoles of octanal, bromine and 2-benzyl-Δ1-pyrroline are reacted each time similarly to the preparation for 69 and 70. The isolated pyrrolizines then are absorbed in 35 ml of absolute benzene and reacted with 105 mmoles (7.7 g) of absolute DMF and 35 mmoles (5.4 g) of POCl$_3$ similarly to the procedure of the Vilsmeier formylation of the diphenyl-2,3-dihydro-1H-pyrrolizines. The two products are separated by column chromatography with silica gel, first elution taking place with n-hexane/diisopropylether 73 and then with diisopropylether 74. Both products will be in the form of oils after the eluates have been concentrated.

Proof of structure for 73: the same product is obtained in the Vilsmeier formylation of 69.

73

Yield: 1.74 g.
C$_{20}$H$_{25}$NO (295.4).
IR: $\nu_{max}$=1660 (C=O), 1610 (C=C) cm$^{-1}$.
$^1$H-NMR: δ(ppm)=0.73-1.07 (m, 3 H, —CH$_3$), 1.07-1.86 (m, 8 H, —CH$_2$—), 2.30-2.70 (m, 2 H, C-2), 2.74-3.05 (m, 4 H, C-1 and Pyr—CH$_2$—), 3.91 (t, 2 H, J=7 Hz, C-3), 7.05-7.46 (m, 5 H, Arom.), 9.87 (s, 1 H, —CHO).

74

Yield: 2.13 g.
C$_{20}$H$_{25}$NO (295.4).
IR: $\nu_{max}$=1655 (C=O), 1610 (C=C) cm$^{-1}$.
$^1$H-NMR: δ(ppm)=0.68-1.01 (m, 3 H, —CH$_3$), 1.01-1.74 (m, 8 H, —CH$_2$—), 2.30-2.67 (m, 2 H, C-2), 2.67-3.00 (m, 4 H, C-1 and Pyr—CH$_2$—), 4.32 (t, 2 H, J=7 Hz, C-3), 7.19-7.46 (m, 5 H, Arom.), 9.67 (s, 1 H, —CHO).

EXAMPLE 75

3-(6(n-HEXYL)-7-PHENYL-2,3-DIHYDRO-1H-PYRROLIZINE-5-YL)-ACRYLIC-ACID ETHYLESTERS (75)

5 mmoles (1.48 g) of 74 are reacted similarly to the procedure for preparing the diphenyl-2,3-dihydro-1H-pyrrolizinyl-acrylic-acid ethylesters. Purification is by column chromatography (silica gel, petroleum ether 50-70/acetic-ester 7+1). Following concentration of the eluate, the production is obtained as an oil Yield 0.45 g (25%).
C$_{24}$H$_{31}$NO$_2$ (365.5).
IR: $\nu_{max}$=1705 (C=O), 1610 (C=C) cm$^{-1}$.
$^1$H-NMR: δ(ppm)=0.62-1.02 (m, 3 H, —CH$_3$), 1.02-1.78 (m, 11 H, —CH$_2$— und —O—CH$_2$—CH$_3$), 2.23-3.01 (m, 6 H, C-2, Pyr—CH$_2$— and C-1), 3.93-4.39 (m, 4 H, C-3 und —O—CH$_2$—), 5.89 (AB, 1 H, J=16.1 Hz, =CH—CO—), 7.04-7.48 (m, 5 H, Arom.), 7.68 (AB, 1 H, J=16.1 Hz, Pry—CH=).

EXAMPLE 76

3-(6-(n-HEXYL)-7-PHENYL-2,3-DIHYDRO-1h-PYRROLIZINE-5-YL)-ACRYLIC ACID (76)

1.0 mmole (0.37 g) of 75 is reacted similarly to the procedure for saponifying the diphenyl-2,3-dihydro-1H-pyrrolizine-acrylic-acid ethylesters.

Yield 0.20 g (59%).
Melting point: 140° C. (with dissociation).
$C_{22}H_{27}NO_2$ (337.5).
IR: $\nu_{max}$3300–2200 (OH), 1670 (C=O), 1595 (C=C) cm$^{-1}$.
$^1$H-NMR (d$_6$-DMSO): δ(ppm)=0.58–0.96 (m, 3 H, —CH$_3$), 0.96–1.60 (m, 8 H, —CH$_2$—), 2.18–2.73 (m, 4 H, C-2 and Pyr—CH$_2$—), 2.86 (t, 2 H, J=7 Hz, C-1), 4.15 (t, 2 H, J=7 Hz, C-3), 5.85 (AB, 1 H, J=15.8 Hz, =CH—CO—), 7.02–7.53 (m, 5 H, Arom.), 7.50 (AB, 1 H, J=15.8 Hz, Pry—CH=).

EXAMPLE 77

6-CYCLOHEXYL-7-PHENYL-2,3-DIHYDRO-1H-PYRROLIZINE (77)

50 mmoles of Br$_2$, dissolved in 10 ml of CCl$_4$, are slowly dripped into the solution of 50 mmoles (6.3 g) of cyclohexylmethylketone in 40 ml of CCl$_4$ with stirring and shielding from light. This batch is then mixed with 50 ml of CH$_2$Cl$_2$ and carefully washed twice with a 5% NaHCO$_3$ solution to neutralize the Hbr. The organic phase is dried by means of Na$_2$SO$_4$ and concentrated. The residue is dissolved in 30 ml of ethanol and reacted with the solution of 50 mmoles of 2-benzyl-Δ1-pyrroline in 20 ml of ethanol. The batch is stirred for 24 h at room temperature. After adding 25 ml of a saturated NaHCO$_3$ solution, stirring proceeds for another 24 h. Then 500 ml of 10% NaCl are added and extraction with ether is carried out twice. The organic phases are dried (Na$_2$SO$_4$). The solvent is distilled and the product is isolated by column chromatography (Al$_2$O$_3$, n-hexane/ether 9+1). The oil (3.0 g) remaining after the eluate was concentrated is impure. It is further reacted without any purification.

EXAMPLE 78

6-CYCLOHEXYL-7-PHENYL-2,3-DIHYDRO-1H-PYRROLIZINE-5YL-CARBALDEHYDE (78)

3.0 g of impure 77 are dissolved in 5 ml of absolute benzene and reacted with 12 mmoles of absolute DMF (0.88 g) and 4 mmoles (0.61 g) of POCl$_3$ similarly to the procedure for the Vilsmeier formylation of the diphenyl-2,3-dihydro-1H-pyrrolizines. Purification is by column chromatography (silica gel, ether/n-hexane 3+1). Then the product is precipitated with ethanol Yield 0.66 g (4.5% referred to the cyclohexylmethyl ketone).
Melting point: 135° C.
$C_{20}H_{23}NO_2$ (293.4).
IR: $\nu_{max}$=1645 (C=O), 1610 (C=C) cm$^{-1}$.
$^1$H-NMR: δ(ppm)=1.01–2.13 (m, 10 H, —CH$_2$— of the cyclohexyl ring), 2.24–3.03 (m, 5 H, C-1, C-2 und Pyr—CH<), 4.35 (t, 2 H, J=7 Hz, C-3), 7.07–7.51 (m, 5 H, Arom.), 9.93 (s, 1 H, CHO).

EXAMPLE 79

3-(6-CYCLOHEXYL-7-PHENYL-2,3-DIHYDRO-1H-PYRROLIZINE-5-YL)-ACRYLIC-ACID ETHYLESTERS (79)

2 mmoles of 78, dissolved in 4 ml of absolute CH$_2$Cl$_2$, are reacted with a solution of 2 mmoles (0.86 g) of ethoxycarbonyl triphenyl phosphonium bromide in 3.5 ml of absolute ethanol and with a solution of Na-ethanolate prepared from 6 mmoles (0.14 g) of sodium and 3 ml of absolute ethanol in a manner similar to the procedure for preparing the diphenyl-2,3-dihydro-1H-pyrrolizinyl acrylic-acid ethylesters. The purification takes place by column chromatography (silica gel, petroleum ether 50–70/acetic-ester 7+2). The oil remaining after concentration solidifies after some time.

Yield: 80 mg (11%).
Melting point: 190° C.
$C_{24}H_{29}NO_2$ (363.5).
IR: $\nu_{max}$=1715 (C=O), 1605 (C=C) cm$^{-1}$.
$^1$H-NMR: δ(ppm)=0.99–1.99 (m, 10 H, —CH$_2$— of the cyclohexyl ring), 1.31 (t, 3 H, J=7 Hz, —O—CH$_2$—CH$_3$) 2.27–2.93 (m, 5 H, C-1, C-2 und Pyr—CH<), 4.17 (t, 2 H, J=7 Hz, C-3), 4.23 (q, 2 H, J=7 Hz, —O—CH$_2$—), 5.85 (AB, 1 H, J=16.2 Hz, =CH—CO—), 7.04–7.48 (m, 5 H, Arom.), 7.91 (AB, 1 H, J=16.2 Hz, Pry—CH=).

EXAMPLE 80

3-(6-CYCLOHEXYL-7-PHENYL-2,3-DIHYDRO-1H-PYRROLIZINE-5-YL)-ACRYLIC ACID (80)

0.22 mmoles (80 mg) of 79 dissolved in 5 ml of ethanol are reacted with 3 ml of 10% aqueous KOH similarly to the procedure for saponifying the diphenyl-2,3-dihydro-1H-pyrrolizine acrylic-acid ethylesters (see p 219).

Yield: 37 mg (50%).
Melting point: 201° C. (with dissociation).
$C_{22}H_{25}NO_2$ (335.4).
IR: $\nu_{max}$=3200–2400 (OH), 1660 (C=O), 1585 (C=C) cm$^{-1}$. $^1$H-NMR: δ(ppm)=0.98 –2.05 (m, 10 H, —CH$_2$— of the cyclohexyl ring), 2.29–2.98 (m, 5 H, C-1, C-2 und Pyr—CH<), 4.21 (t, 2 H, J=7 Hz, C-3), 5.87 (AB, 1 H, J=16.0 Hz, =CH—CO—), 7.02–7.55 (m, 5 H, Arom.), 8.01 (AB, 1 H, J=16.0 Hz, Pry—CH=).

GENERAL PROCEDURE FOR THE N-ALKYLATION OF 2-METHYL-3,4-DIPHENYLPYRROLE 2 mmoles (0.47 g) of 2-methyl-3,4-diphenyl-pyrrole (AUST. J. CHEM. 1966, 19, pp 1871–1885) [and] 2.2 mmoles of p-toluene sulfonic-acid methylester (in 81b) or alkylbromide (for the remaining compounds) and 1 mmole (0.32) g) of tetrabutylammonium bromide are mixed with 10 ml ether and 5 ml of 50% aqueous NaOH. While agitating strongly, the mixture is heated for 8 h to slow boiling. Thereupon the batch is poured into 100 ml of H$_2$O and extracted twice with ether. The ether phases are washed with 1% H$_3$PO$_4$ and H$_2$O, dried by means of Na$_2$SO$_4$ and concentrated. The product isolation takes place by column chromatography (Al$_2$O$_3$, n-hexane/ether 9+1).

The compounds so obtained and their physical properties are listed in Table 12 below.

EXAMPLE 88

1-NEOPENTYL-2-METHYL-3,4-DIPHENYLPYRROLE (81i)

The above compound cannot be synthesized. However it may be prepared as follows:

2 mmoles (0.46 g) of 2-methyl-3,4-diphenyl-pyrrole, 2.6 mmoles of potassium-t-butylate and 3 mmoles (0.45 g) of neopentyl bromide in 6 ml of absolute DMSO are heated for 45 minutes to 130°–140° C. Following cooling, 100 ml $H_2O$ are added, acidification with dilute $H_3PO_4$ and next double extraction with ether are carried out. The ether phases are washed with $H_2O$, dried by means $Na_2SO_4$, and concentrated. The product is isolated from the residue by column chromatography ($Al_2O_3$, n-hexane/ether 9+1) and precipitated with ethanol (similarly to the case for 81h).

Yield: 0.31 g (51%).
Melting point: 132° C.
$C_{22}N_{25}N$ (303.4) COMPUTED C 87.1 H 8.30 N 4.6.
MEASURED C 86.9 H 8.21 N 4.5.
IR: $\nu_{max}=1605$ (C=C) cm$^{-1}$.
MS: m/z (rel. Int.)= 303 (89%, M+), 288 (9%, M+-$CH_3$, 273.74), 247 (58%, M+-$C_4H_8$, 201.34), 246 (100%, 247-H).
$^1$H-NMR: δ(ppm) = 1.02 (s, 9 H, —$CH_3$), 2.19 (s, 3 H, Pyr—$CH_3$), 3.66 (s, 2 H, >N—$CH_2$—), 6.75 (s, 1 H, C-5), 7.06–7.33 (m, 10 H, Arom.).

TABLE 12

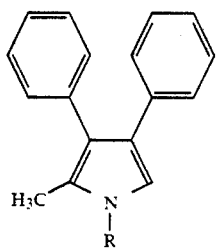

| EXAMPLE Nr. | R | | MELTING POINT °C. | IR (C=C) |
|---|---|---|---|---|
| 81[1)] | $CH_3$ | 81b | | |
| 82 | $C_2H_5$ | 81c | | 1600 |
| 83 | n-$C_3H_7$ | 81d | 80 | 1605 |
| 84 | n-$C_4H_9$ | 81e | | 1610 |
| 85[2)] | n-$C_5H_{11}$ | 81f | | |
| 86[2)] | n-$C_6H_{13}$ | 81g | | |
| 87 | iso-$C_4H_9$ | 81h | 116 | 1605 |

[1)]Tetrahedron Lett. 1969, 55, 4875–4878
Chem. Pharm. Bull. 1974, 22, 61–69
[2)]mixture with alkyl bromide; it is reacted without further purification

GENERAL PROCEDURE FOR PREPARING THE 3-(5-METHYL-3,4-DIPHENYLPYRROLE-2-YL)-PROPIONIC-ACID METHYLESTERS 1 mmole of 2-methyl-3,4-diphenylpyrrole or of 1-alkyl-2-methyl-3,4-diphenylpyrrole 82b-i and 1.5 mmoles (0.13 g) of acrylic-acid methylester are dissolved in 4 ml of dichloroethane. Following addition of 0.06 ml of $BF_3$-ethylether complex, the batch is stirred for 1 h at room temperature and after 15 minutes in each case again the same amounts of acrylic-acid methylester and $BF_3$-ethylester complex are added. Then the batch is mixed with 50 ml of $H_2O$ and extraction with ether is performed twice. The ether phases are washed with $H_2O$, dried by means of $Na_2SO_4$ and concentrated. The product is isolated from the residue by column chromatography ($Al_2O_3$, n-hexane/ether 1+4(82a) or 1+1 (82b,c) or 3+2 (remaining compounds)). After the eluate has been concentrated, an oil remains.

The compounds so obtained and several of their physical properties are listed in Table 13 below.

GENERAL PROCEDURE FOR THE SAPONIFICATION OF THE 3-5-METHYL-3,4-DIPHENYLPYRROLE-2-YL)-PROPIONIC-ACID METHYLESTERS

The solution of 0.4 mmoles of 3-(2-methyl-3,4-diphenylpyrrole-5-yl)-propionic-acid methylester 82a or 3-(1-alkyl-2-methyl-3,4-diphenylpyrrole--5-yl)-propionic-acid methylester 82b-i in 3 ml of ethanol is heated to boiling. 2 ml of 10% aqueous KOH previously degassed by boiling are dripped into the batch which then is heated with reflux for another 5 minutes. Following cooling, the batch is poured into 100 ml of 5% NaCl solution and is washed twice with 50 ml of ether. The aqueous phase is acidified with dilute $H_3PO_4$ and extracted twice with 50 ml of ether. The ether phases are washed with 100 ml of $H_2O$ and dried by means of $Na_2SO_4$. The solvent is distilled, and where called for the product is precipitated with hexane.

The compounds so obtained and several of their physical properties are shown in Table 14.

TABLE 13

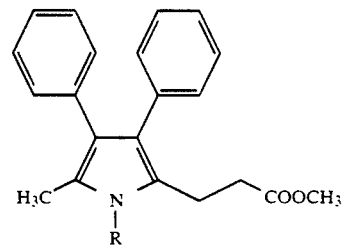

| EXAMPLE Nr. | R | | IR (C=O) |
|---|---|---|---|
| 89 | H | 82a | 1730 |
| 90 | $CH_3$ | 82b | 1740 |
| 91 | $C_2H_5$ | 82c | 1740 |
| 92 | n-$C_3H_7$ | 82d | 1740 |
| 93 | n-$C_4H_9$ | 82e | 1745 |
| 94 | n-$C_5H_{11}$ | 82f | 1740 |
| 95 | n-$C_6H_{13}$ | 82g | 1740 |
| 96 | iso-$C_4H_9$ | 82h | 1740 |
| 97 | Neopentyl | 82i | 1740 |

TABLE 14

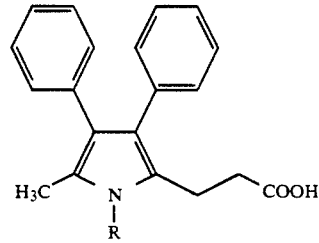

| EXAMPLE Nr. | R | MELTING POINT °C. | IR (C=O) |
|---|---|---|---|
| 98 | H | 60 | 1710 |
| 99 | $CH_3$ | 108 | 1710 |
| 100 | $C_2H_5$ | 157 | 1715 |
| 101 | n-$C_3H_7$ | 128 | 1705 |

TABLE 14-continued

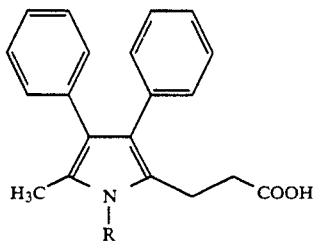

| EXAMPLE Nr. | R | MELTING POINT °C. | IR (C=O) |
|---|---|---|---|
| 102 | n-C4H9 | >49° (dissoc.) | 1715 |
| 104 | n-C5H11 | — | 1715 |
| 105 | n-C6H13 | — | 1715 |
| 106 | iso-C4H9 | 50 | 1715 |
| 107 | Neopentyl | 48 | 1710 |

GENERAL PROCEDURE FOR THE N-ALKYLATION OF 5-METHYL-2,3-DIPHENYLPYRROLE 5 mmoles (1.17 g) of 5-methyl-2,3-diphenylpyrrole (AUST. J. CHEM. 1966, 19, pp 1871–1885), 5.5 mmoles of toluene sulfonic-acid methylester or of alkyl bromide and 1 mmole (032 g) of tetrabutyl ammonium bromide are mixed with 10 ml ether and 5 ml of 10% aqueous NaOH. The reaction henceforth is carried out in the manner of the procedure for the N-alkylation of 2-methyl-3,4-diphenylpyrrole.

The compounds so obtained and some of their physical properties are shown in Table 15.

GENERAL PROCEDURE FOR PREPARING THE (5-METHYL-4,5-DIPHENYLPYRROLE-3-YL)-ACETIC-ACID ETHYLESTERS 2.5 mmoles of methyl-2,3-diphenylpyrrole (AUST. J. CHEM. 1966, 19, pp 1871–1885) or of 1-alkyl-5-methyl-2,3-diphenylpyrrole 84b-j, dissolved in 2 ml of absolute toluene, are reacted similarly to the procedure for preparing the diphenyl-2,3-dihydro-1H-pyrrolizine-acetic-acid ethylesters. Following column chromatography (silica gel, n-hexane/ether 1+1 in Example 117 or Al2O3, n-hexane-ether 9+1 in the remaining compounds), the products are obtained in the form of oils.

The compounds so obtained and the infra-red data relation to them are shown in Table 16.

TABLE 15

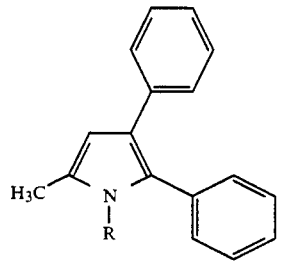

| EXAMPLE Nr. | R | MELTING PT. °C. | IR (C=C) |
|---|---|---|---|
| 108 | CH3 | 84b 149 | 1605 |
| 109 | C2H5 | 84c 68–69 | 1605 |
| 110 | n-C3H7 | 84d — | 1605 |
| 111 | n-C4H9 | 84e — | 1605 |

TABLE 15-continued

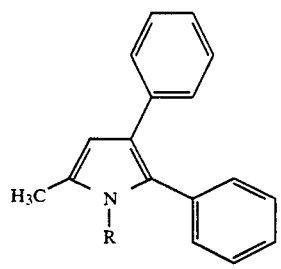

| EXAMPLE Nr. | R | MELTING PT. °C. | IR (C=C) |
|---|---|---|---|
| 112 | n-C5H11 | 84f | 1605 |
| 113 | n-C6H13 | 84g | 1605 |
| 114 | n-C8H17[1] | 84h | |
| 115 | iso-C4H9 | 84i 107 | 1600 |
| 116 | Neopentyl | 84j 89 | 1605 |

[1] mixture with n-C8H17Br, reacted without further purification

TABLE 16

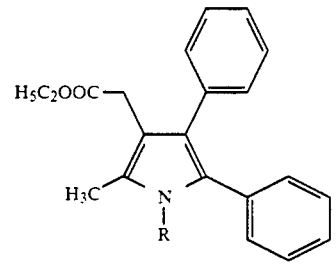

| EXAMPLE Nr. | R | | IR (C=O) |
|---|---|---|---|
| 117 | H | 85a | 1730 |
| 118 | CH3 | 85b | 1740 |
| 119 | C2H5 | 85c | 1735 |
| 120 | n-C3H7 | 85d | 1740 |
| 121 | n-C4H9 | 85e | 1735 |
| 122 | n-C5H11 | 85f | 1740 |
| 123 | n-C6H13 | 85g | 1740 |
| 124 | n-C8H17 | 85h | 1740 |
| 125 | iso-C4H9 | 85i | 1735 |
| 126 | Neopentyl | 85j | 1735 |

GENERAL PROCEDURE FOR SAPONIFYING THE (2-METHYL-4,5-DIPHENYLPYRROLE-3-YL)-ACETIC-ACID ETHYLESTERS

The solution of 0.6 mmoles of (2-methyl-4,5-diphenylpyrrole-3-yl)-acetic-acid ethylester or of (1-alkyl-2-methyl-4,5-diphenylpyrrole-3-yl)-acetic-acid ethylester in 5 ml of ethanol is heated to boiling. Then 3 ml of 10% aqueous KOH previously degassed by boiling are dripped into the batch which is further heated for 1 h with reflux. Following cooling the batch is poured into 100 ml of 5% NaCl solution and the mixture is then acidified with 8% H3PO4 and extracted three times with ether. The organic phases are dried by means of Na2SO4 and concentrated. Production purification takes place by column chromatography (silica gel, 1st n-hexane/ether 1+1 in The Examples 127–131, or 2+1 in Examples 132–136, 2nd ether). The eluates are concentrated down to a few ml. After adding n-hexane and concentrating again, the product precipitates.

The compounds so obtained and their physical data are shown in Table 17.

TABLE 17

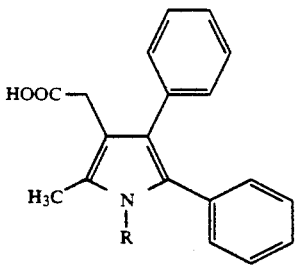

| EXAMPLE Nr. | R | | MELTING POINT °C. | IR (C=O) |
|---|---|---|---|---|
| 127 | H | 86a | 110 | 1710 |
| 128 | CH$_3$ | 86b | 161 | 1710 |
| 129 | C$_2$H$_5$ | 86c | 177 | 1705 |
| 130 | n-C$_3$H$_7$ | 86d | 172 | 1700 |
| 131 | n-C$_4$H$_9$ | 86e | 129 | 1705 |
| 132 | n-C$_5$H$_{11}$ | 86f | 121 | 1710 |
| 133 | n-C$_6$H$_{13}$ | 86g | 127 | 1710 |
| 134 | n-C$_8$H$_{17}$ | 86h | 45 | 1715 |
| 135 | iso-C$_4$H$_9$ | 86i | 168 | 1710 |
| 136 | Neopentyl | 86j | 163 | 1710 |

GENERAL PROCEDURE FOR PREPARING THE 6-ARYL-7-PHENYL-2,3-DIHYDRO-1H-PYRROLIZINES OR THE 6-PHENYL-7-ARYL-2,3-DIHYDRO-1H-PYRROLIZINES 20 mmoles of aromatics-substituted* or unsubstituted α-bromo-acetophe-none dissolved in 25 ml of CH$_2$Cl$_2$ are mixed with the solution of 20 mmoles of unsubstituted or aromatics-substituted** resp. 2-benzyl-Δ1-pyrroline in 50 ml of ethanol and are stirred for 24 h at room temperature. Then 20 ml of saturated aqueous NaHCO$_3$ solution are added and the batch is stirred for another 24 h at room temperature. The batch is poured into 500 ml of 5% NaCl solution and is extracted three times each time with 100 ml of ether/CH$_2$Cl$_2$ 3+1. The organic phases are dried by means of Na$_2$SO$_4$ and processed in the manner discussed below.

*α-bromo-3-chloroacetophenone, α-bromo-3,4-dimethoxyacetophenone, α-bromo-3,4-dichloroacetophenone and α-bromo-4-phenoxyacetophenone are not available commercially. They are prepared as follows:

A solution of 20 mmoles (3.2 g) of bromine in 10 ml of CH$_2$Cl$_2$ is slowly dripped into the solution of 20 mmoles of 3-chloroacetophenone, 3,4-dimethoxyacetophenone, 3,4-dichloroacetophenone or 4-phenoxyacetophenone in 15 ml of CH$_2$Cl$_2$ and 20 ml of dioxan. Thereupon the batch is mixed with 50 ml of CH$_2$Cl$_2$ and carefully washed twice with 5% NaHCO$_3$ solution to remove the Hbr. The organic phase is dried by means of Na$_2$SO$_4$ and concentrated. The residue is reacted directly as described above with 20 mmoles of 2-benzyl-Δ1-pyrroline.

**2-(4-chlorobenzyl)-Δ1-pyrroline:

The preparation is similar to that for 2-benzyl-Δ1-pyrroline (J. AMER. CHEM. SOC. 1932, 54, pp 3971–3976)

**2-(4-methylbenzyl)-Δ1-pyrroline:

A Grignard reagent is prepared from 0.15 moles (3.6 g) of Mg and 0.15 moles (21.1 g) of methylbenzyl chloride in 150 ml of absolute ether. After dripping 0.15 moles (15.5 g) of 4-chlorobutyronitrile dissolved in 100 ml absolute ether into the batch, same is heated for 2 h to reflux. Next the ether is distilled and 200 ml of absolute xylene are added. After further boiling with reflux for 2 h, the batch is mixed with 100 ml of H$_2$O while being ice-cooled and is acidified with dilute H$_3$PO$_4$. The aqueous phase is made alkaline with concentrated NH$_3$ and ice-cooling and the generated precipitate is evacuated. The filtrate is extracted three times with 50 ml of CH$_2$Cl$_2$ and the precipitate is washed with 100 of CH$_2$Cl$_2$. The CH$_3$Cl$_2$ solutions are combined, dried by means of Na$_2$SO$_4$ and concentrated. The product is isolated from the last residue by distillation (boiling point 117° C. at 0.1 torr). Yield 3.7 g (14%). C$_{12}$H$_{15}$N (173.3). Ir:$\nu_{max}$=1640 (C=N), 1605 (C=C)/cm.

**2-(4-methoxybenzyl)-Δ1-pyrrolline:

4-methoxybenzyl magnesium chloride is prepared from 3.0 moles (72.9 g) of Mg and 0.15 moles (23.5 g) of 4-methoxybenzylchloride in 500 ml of absolute ether. The product is reacted further with 0.15 moles (15.5 g) of 4-chlorobutyronitrile and is purified by distillation (boiling point 142 C. at 0.1 torr). Yield 2.4 g (8%). C$_{12}$H$_{15}$NO (189.3). Ir: $\nu_{max}$=1640 (C=N), 1610 (C=C)/cm.

GENERAL PROCEDURE FOR PREPARING 3-(6-CHLOROPHENYL-AND 6-NITROPHENYL-7-PHENYL-2,3-DIHYDRO-1H-PYRROLIZINE-5-YL)-PROPIONIC-ACID METHYLESTERS 4 mmoles of 6 chloro- or 6-nitrophenyl-7-phenyl-2,3-dihydro-1H-pyrrolizine and 6 mmoles (0.52 g) of acrylic-acid methylester are dissolved in 16 ml of absolute dichloroethane. After adding 0.24 ml of BF$_3$ ethylene complex, the batch is stirred for 1 h at room temperature, and the same amounts of acrylic-acid methylester and BF$_3$ ethylether complex are added in each case again after 15 minutes. Thereupon the batch is poured into 100 ml of 10% NaCl solution and is extracted twice with ether/CH$_2$Cl$_2$ 3+1. The organic phases are dried by means of Na$_2$SO$_4$ and concentrated. The residue then is processed in the manner discussed below.

GENERAL PROCEDURE FOR SAPONIFYING THE 3-(6-CHLOROPHENYL-AND 6-NITROPHENYL-7-PHENYL-2,3-DIHYDRO-1H-PYRROLIZINE-6-YL)-PROPIONIC-ACID METHYLESTERS

The solution of 1 mmole of the corresponding pyrrolizinyl-propionic-acid methylester in 10 ml of ethanol is heated to boiling. 5 ml of 10% aqueous KOH solution previous degassed is dripped into the batch which is then heated another 5 minutes with reflux. Following cooling the batch is poured into 100 ml of 5% NaCl solution and acidified with 8% H$_3$PO$_4$ and extracted three times with ether/CH$_2$Cl$_2$ 3+1. The organic phases are dried by means of Na$_2$SO$_4$, concentrated, and processed in the manner described above.

GENERAL PROCEDURE FOR THE VILSMEIER FORMYLATION OF AROMATICS-SUBSTITUTED 6,7-DIPHENYL-2,3-DIHYDRO-1H-PYRROLIZINES 6 mmoles of the corresponding pyrrolizine dissolved in 6 ml of absolute benzene are reacted with 18 mmoles (1.32 g) of absolute DMF and 6 mmoles (0.92 g) of POCl$_3$ similarly to the procedure for the Vilsmeier formylation of the diphenyl-2,3-dihydro-1H-pyrrolizines.

GENERAL PROCEDURE FOR PREPARING AROMATICS-SUBSTITUTED 6,7-DIPHENYL-2,3-DIHYDRO-1H-PYROLLIZINYL-ACRYLIC-ACID ETHYLESTERS 2.5 mmoles of the corresponding carbaldehyde dissolved in 5 ml of absolute $CH_2Cl_2$ are reacted with the solution of 2.5 mmoles (1.08 g) of ethoxycarbonyl-methyltriphenyl-phosphonium bromide in 4 ml of absolute ethanol and with a solution of Na-ethanolate prepared from 7.5 mmoles (0.17 g) of sodium and 3 ml of absolute ethanol in a manner similar to the procedure for preparing the diphenyl-2,3-dihydro-1H-pyrrolizinyl-acrylic-acid ethylesters.

GENERAL PROCEDURE FOR SAPONIFYING AROMATICS-SUBSTITUTED 3-(6-7-DIPHENYL-2,3-DIHYDRO-1H-PYRROLIZINE-5-YL)-ACRYLIC-ACID ETHYLESTERS.

1.2 mmoles of the corresponding pyrrolizinyl-acrylic-acid ethylesters dissolved in 50 ml of ethanol are reacted with 10 ml of aqueous KOH similarly to the procedure for saponifying the 3-(diphenyl-2,3-dihydro-1H-pyrrolizine-5-yl)-acrylic-acid ethylesters.

GENERAL PROCEDURE FOR HYDROGENATING AROMATICS-SUBSTITUTED 3-(6,7-DIPHENYL-2,3-DIHYDRO-1H-PYRROLIZINE-5-YL) ACRYLIC ACIDS 0.9 mmoles of the corresponding pyrrolizinyl acrylic acid are dissolved in 30 ml of absolute THF. After adding 10 ml of absolute ethanol and a spatula tip-ful of $PtO_2$ (alternatively, palladium also may be used), hydrogenation is carried out in the autoclave for about 4 h at 15 bars. Several times a spatula tip-ful of fresh $PtO_2$ (or palladium) is added. Upon complete reaction (thin-layer chromatography: silica gel, THF), the catalyst is evacuated, the solvent is distilled and the product is isolated.

GENERAL PROCEDURE FOR SPLITTING THE ARYLMETHYLETHERS 0.5 mmoles of the corresponding methyl compound dissolved in 5 ml of absolute $CH_2Cl_2$ are dripped into the solution of 0.20 ml of $BBr_3$ in 3 ml of absolute $CH_2Cl_2$ at $-80°$ C. The mixture is allowed to rise to room temperature in about 8 h. After adding 30 ml of $H_2O$, extraction is carried out three times with ether. The organic phases are washed twice with a saturated NaCl solution, dried by means of $Na_2SO_4$ and are processed.

The compounds so obtained and their physical properties are shown in the Tables 18 through 27 below.

TABLE 18

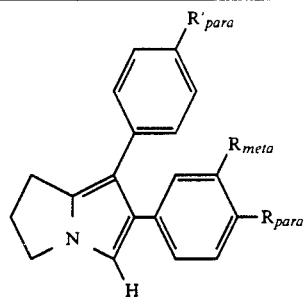

| EXAMPLE Nr. | $R_{meta}$ | $R_{para}$ | $R'_{para}$ | MELT. PT. °C. | IR (C=C) |
|---|---|---|---|---|---|
| 138 | Cl | H | H |  | 1600 |
| 139[1] | H | Cl | H |  | 1605 |
| 140 | $NO_2$ | H | H | 117 | 1605 |
| 141 | H | $NO_2$ | H | 132 | 1595 |
| 142 | H | H | Cl | 156 | 1605 |

[1] Chemiker-Zeitung 1986, 110, 267-271

TABLE 19

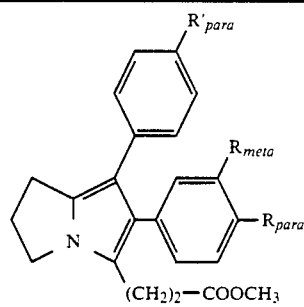

| EXAMPLE Nr. | $R_{meta}$ | $R_{para}$ | $R'_{para}$ | MELTING PT. °C. | IR (C=O) |
|---|---|---|---|---|---|
| 143 | Cl | H | H | 99 | 1735 |
| 144 | H | Cl | H | 98 | 1730 |
| 145 | $NO_2$ | H | H |  | 1740 |
| 146 | H | $NO_2$ | H |  | 1740 |
| 147 | H | H | Cl | 111 | 1730 |

TABLE 20

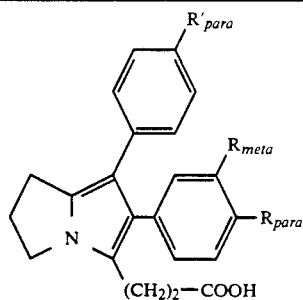

| EXAMPLE Nr. | $R_{meta}$ | $R_{para}$ | $R'_{para}$ | MELT. PT. °C. | IR (C=O) |
|---|---|---|---|---|---|
| 143 | Cl | H | H | 99 | 1735 |
| 144 | H | Cl | H | 98 | 1730 |
| 145 | $NO_2$ | H | H |  | 1740 |
| 146 | H | $NO_2$ | H |  | 1740 |
| 147 | H | H | Cl | 111 | 1730 |

TABLE 21

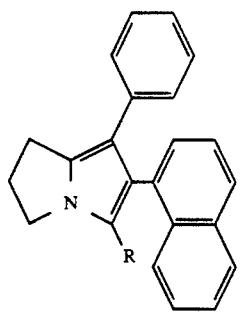

| EXAMPLE Nr. | R | MELT. PT. °C. | IR (C=O) |
|---|---|---|---|
| 153 | H | | 1605 (C=C) |
| 154 | CHO | >84 | 1650 |
| 155 | CH=CHCOOC$_2$H$_5$ (E) | 122 | 1715 |
| 156 | CH=CHCOOH (E) | 229 | 1660 |
| 157 | (CH$_2$)$_2$COOH | 157 | 1710 |

TABLE 22

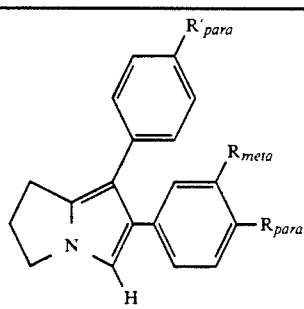

| EXAMPLE Nr. | R$_{meta}$ | R$_{para}$ | R'$_{para}$ | MELT. PT. °C. | OR (C=C) |
|---|---|---|---|---|---|
| 158 | CH$_3$ | H | H | | 1605 |
| 159 | H | CH$_3$ | H | | 1605 |
| 160 | OCH$_3$ | H | H | | 1605 |
| 161[1] | H | OCH$_3$ | H | | |
| 162[1] | OCH$_3$ | OCH$_3$ | H | | |
| 163[2] | H | O—C$_6$H$_5$ | H | | |
| 164 | Cl | Cl | H | 119 | 1605 |
| 165 | H | H | CH$_3$ | 104 | 1610 |
| 166 | H | H | OCH$_3$ | | 1605 |

[1] Chemiker-Zeitung 1986 110, 267-271
[2] the product is impure; it is made to react without further purification

TABLE 23

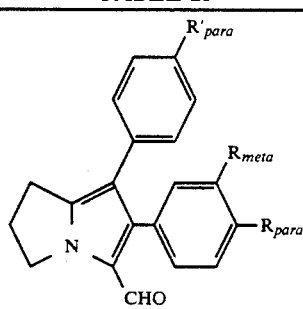

| EXAMPLE Nr. | R$_{meta}$ | R$_{para}$ | R'$_{para}$ | MELT. PT. °C. | IR (C=O) |
|---|---|---|---|---|---|
| 167 | CH$_3$ | H | H | 128 | 1645 |
| 168 | H | CH$_3$ | H | 142 | 1645 |

TABLE 23-continued

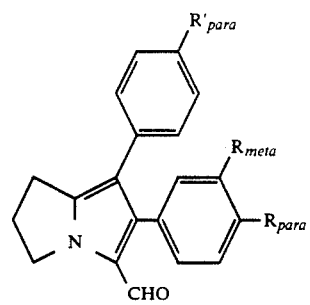

| EXAMPLE Nr. | R$_{meta}$ | R$_{para}$ | R'$_{para}$ | MELT. PT. °C. | IR (C=O) |
|---|---|---|---|---|---|
| 169 | OCH$_3$ | H | H | 117 | 1635 |
| 170[1] | H | OCH$_3$ | H | | |
| 171[1] | OCH$_3$ | OCH$_3$ | H | | |
| 172 | H | O—C$_6$H$_5$ | H | 135 | 1635 |
| 173 | Cl | Cl | H | 162 | 1640 |
| 174 | H | H | CH$_3$ | 102 | 1645 |

[1] Chemiker-Zeitung 1986 110, 267-271

TABLE 24

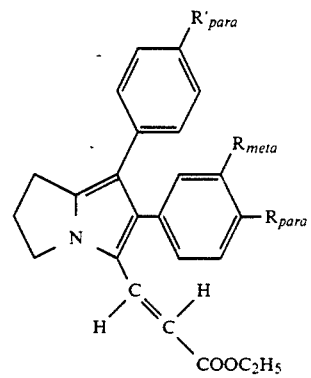

| EXAMPLE Nr. | R$_{meta}$ | R$_{para}$ | R'$_{para}$ | MELT. PT. °C. | IR (C=O) |
|---|---|---|---|---|---|
| 175 | CH$_3$ | H | H | 142 | 1710 |
| 176 | H | CH$_3$ | H | 158 | 1710 |
| 177 | OCH$_3$ | H | H | 119 | 1710 |
| 178 | H | OCH$_3$ | H | 164 | 1705 |
| 179 | OCH$_3$ | OCH$_3$ | H | 133 | 1705 |
| 180 | H | O—C$_6$H$_5$ | H | 173 | 1705 |
| 181 | Cl | Cl | H | 122 | 1715 |
| 182 | H | H | CH$_3$ | 222 | 1705 |

TABLE 25

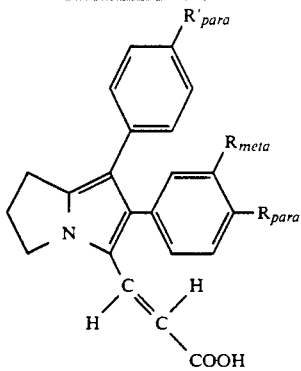

| EXAMPLE Nr. | $R_{meta}$ | $R_{para}$ | $R'_{para}$ | MELTING PT. °C. | IR (C=O) |
|---|---|---|---|---|---|
| 183 | CH₃ | H | H | 216 | 1660 |
| 184 | H | CH₃ | H | 221 | 1680 |
| 185 | OCH₃ | H | H | 205 | 1670 |
| 186 | H | OCH₃ | H | 216 | 1675 |
| 187 | OCH₃ | OCH₃ | H | 216 | 1660 |
| 188 | H | O—C₆H₅ | H | 221 | 1660 |
| 189 | Cl | Cl | H | 229 | 1660 |
| 190 | H | H | CH₃ | 118 | 1665 |

TABLE 26

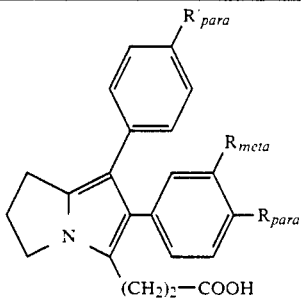

| EXAMPLE Nr. | $R_{meta}$ | $R_{para}$ | $R'_{para}$ | MELT. PT. °C. | IR (C=O) |
|---|---|---|---|---|---|
| 191 | CH₃ | H | H | 125 | 1710 |
| 192 | H | CH₃ | H | 122 | 1710 |
| 193 | OCH₃ | H | H | 111 | 1710 |
| 194 | H | OCH₃ | H | 73 | 1710 |
| 195 | OCH₃ | OCH₃ | H | 152 | 1725 |
| 196 | OH | H | H | 87 | 1710 |
| 197 | H | OH | H | 187 | 1700 |
| 198 | OH | OH | H | 76 | 1710 |
| 199 | H | O—C₆H₅ | H | 178 | 1705 |
| 200 | Cl | Cl | H | 144 | 1710 |
| 201 | H | H | CH₃ | 182 | 1705 |

TABLE 27

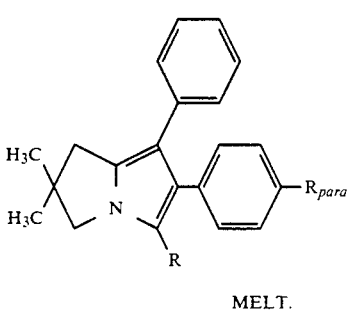

| EXAMPLE Nr. | R | $R_{para}$ | MELT. PT. °C. | IR (C=O) |
|---|---|---|---|---|
| 202 | H | Cl | 118 | 1605 (C=C) |
| 203 | (CH₂)₂COOCH | Cl | 113 | 1735 |
| 204 | (CH₂)₂COOH₃ | Cl | 207 | 1710 |

EXAMPLE 205

2,2-DIMETHYL-6-(4-FLUORO)-7-PHENYL-2,3-DIHYDRO-1H-PYRROLIZINE(1v)

20 mmoles of α-chlorine-4-fluoroacetophenone dissolved in 25 ml of CH₂Cl₂ are mixed with the solution of 20 mmoles of 2-benzyl-4,4-dimethyl-Δ1-pyrroline 25 ml of ethanol and the batch is stirred for 24 h at a bath temperature of 70° C. Thereupon 20 ml of saturated aqueous NAHCO₃ solution is added and agitation continues for another 24 h at the same temperature. The batch is poured into 500 ml of 5% NaCl solution and is then extracted three times each time with 100 ml of ether/CH₂Cl₂ 3+1. The organic phases are dried by means of Na₂SO₄. The product is precipitated by column chromatography (Al₂O₃, n-hexane/ether 9+1) in the form of an oil Yield 3.1 g (51%).
C₂₁H₂₀FN (305.4).
IR: $\nu_{max}$=1605 (C=C) cm⁻¹.
¹H-NMR: δ(ppm)=1.28 (s, 6H, —CH₃), 2.78 (s, 2H, C-1), 3.71 (s, 2H, C-3), 6.64 (s, 1H, C-5), 6.75–7.60 (m, 9H, Arom.).

EXAMPLE 206

2,2-DIMETHYL-6-(4-FLUORO)-7-PHENYL-2,3-DIHYDRO-1H-PYRROLOZINE-5-YL-CARBALDEHYDE (6v)

19 mmoles of iv dissolved in 9 ml of absolute benzene are reacted with 27 mmoles (1.97 g) of absolute DMF and 9 mmoles (1.38 g) of POCl₃ in a manner similar to the Vilsmeier formylation of the diphenyl-2,3-dihydro-1H-pyrrolines. Purification is by means of column chromatography (silica gel, n-hexane/ether 2+1). When the eluates are concentrated, the product precipitates.

Yield: 0.9 g (30%)
Melting point: 186° C.
C₂₂H₂₀FNO (333.4).
IR: $\nu_{max}$=1645 (C=O), 1610 (C=C) cm⁻¹.
¹H-NMR: δ(ppm)=1.33 (s, 6H, —CH₃), 2.83 (s, 2H, C-1), 4.18 (s, 2H, C-3), 6.90–7.44 (m, 9H, Arom.), 9.38 (s, 1H, —CHO).

EXAMPLE 207

3-(2,2-DIMETHYL-6-(4-FLUORO-7-PHENYL-2,3-DIHYDRO-1H-PYRROLIZINE-5-YL)-ACRYLIC-ACID ETHYLESTERS (34v)

2 mmoles of 6v dissolved in 15 ml of absolute CH₂Cl₂ are reacted with the solution of 2 mmoles (0.86 g) of ethoxycarbonyl methyltriphenylphosphonium bromide in 4 ml of absolute ethanol and a solution of Na-ethanolate prepared from 6 mmoles (0.14 g) sodium and 3 ml absolute ethanol in a manner similar to the procedure for preparing the diphenyl-2,3-dihydro-1H-pyrrolizinyl acrylic-acid ethylester. Purification is by column chromatography (silica gel, CH₂Cl₂). After the eluates have been concentrated, the product remains in the form of a foam.

Yield: 0.33 g (41%).

Melting point: 152° C.
C$_{26}$H$_{26}$FNO$_2$ (403.5).
IR: $\nu_{max}$=1715 (C=O), 1620 (C=C) cm$^{-1}$.
$^1$H-NMR: δ(ppm)=1.27 (t, 3H, J=7 Hz, —O—CH$_2$—CH$_3$), 1.33 (s, 6H, —CH$_3$), 2.86 (s, 2H, C-1), 4.00 (s, 2H, C-3), 4.19 (q, 2H, J=7 Hz, —O—CH$_2$—CH$_3$), 5.90 (AB, 1H, J=16.4 Hz, =CH—CO—), 6.87-7.34 (m, 9H, Arom.), 7.48 (AB, 1H, J=16.4 Hz, Pyr—CH=).

EXAMPLE 208

3-(2,2-DIMETHYL-6(4-FLUORO)-7-PHENYL-2,3-DIHYDRO-1H-PYRROLIZINE-5-YL) ACRYLIC-ACID (35v)

0.6 mmoles of 34v dissolved in 30 ml of ethanol are reacted with 6 ml of 10% aqueous KOH in a manner similar to the saponification of the diphenyl-2,3-dihydro-1H-pyrrolizinyl acrylic-acid esters.
Yield 0.20 g(89%).
Melting point: 242° C.
IR: $\nu_{max}$=3300-2200 (OH), 1685, 1670 (C=O), 1600 (C=C) cm$^{-1}$.
$^1$H-NMR (d$_6$-DMSO): δ(ppm)=1.27 (s, 6H, —CH$_3$), 2.84 (s, 2H, C-1), 4.06 (s, 2H, C-3), 5.92 (AB, 1H, J=16.4 Hz, =CH—CO—), 6.87-7.41 (m, 9H, Arom. and Pyr—CH=).

EXAMPLE 209

3-(2,2-DIMETHYL-6-(FLUORO)-PHENYL-2,3-DIHYDRO-1H-PYRROLIZINE-5-YL)-PROPIONIC ACID (27v)

0.3 mmoles of 27v are reacted int he manner of the procedure for hydrogenating the aromatics-substituted 3-(6,7-diphenyl-2,3-dihydro-1H-pyrrolizine-5-yl)-acrylic-acids. Palladium is used as the catalyst. The product is precipitated by means of hexane.
Yield: 0.08 g (71%).
Melting point: 182° C.
C$_{24}$H$_{24}$FNO$_2$(377.5): COMPUTED: C 76.4; H 6.41; N 3.7. MEASURED: C 75.8; H 6.56; N 3.3.
IR: $\nu_{max}$=3300-2400 (OH), 1710 (C=O), 1605 (C=C) cm$^{-1}$.
$^1$H-NMR: δ(ppm)=1.30 (s, 6H, —CH$_3$), 2.28-2.58 (m, 2H, —CH$_2$—CO—), 2.73-3.03 (m, 2H, Pyr—CH$_2$—), 2.81 (s, 2H, C-1), 3.68 (s, 2H, C-3), 6.76-7.28 (m, 9H, Arom.).

EXAMPLE 210

2,2-DIMETHYL-6-(4-PHENOXYPHENOL)-7-PHENYL-2,3-DIHYDRO-1H-PYRROLIZINE (1w)

20 mmoles of 2 benzyl-4,4-dimethyl-δ1-[pyrroline 1b$_3$ are reacted with 20 mmoles of α-bromo-4-chloroacetophenone in 50 ml of ethanol similarly to the procedure for preparing the 6-aryl-7-phenyl-2,3-dihydro-1H-pyrrolizines. Purification is by column chromatography (Al$_2$O$_3$, n-hexane/ether 9+1). Following concentration of the eluates, 1w remains in the form of oil
Yield: 2.7 g(36%).
C$_{27}$H$_{25}$NO (379.5).
IR: $\nu_{max}$=1605 und 1595 (C=C) cm$^{-1}$.
$^1$H-NMR: δ(ppm)=1.28 (s, 6H, —CH$_3$), 2.78 (s, 2H, C-1), 3.71 (s, 2H, C-3), 6.65 (s, 1H, C-5), 6.78-7.57 (m, 14H, Arom.).

EXAMPLE 211

2,2-DIMETHYL-6-(4-PHENOXYPHENYL)-7-PHENYL-2,3-DIHYDRO-1H-PYRROLIZINE-5-YL-CARBALDEHYDE (6w)

5 mmoles of 1w dissolved in 6 ml of absolute benzene are reacted with 18 mmoles (1.32 g) of absolute DMF and 6 mmoles (0.92 g) of POCl$_3$ similarly to the procedure for the Vilsmeier formylation of the diphenyl-2,3-dihydro-1H-pyrrolizines. Purification is by column chromatography (silica gel, CH$_2$Cl$_2$). The product is precipitated by ethanol.
Yield: 0.94 g (38%).
Melting point: 139° C.
C$_{28}$H$_{25}$NO$_2$ (407.5).
IR: $\nu_{max}$=1645 (C=O), 1605 und 1590 (C=C)cm$^{-1}$.
$^1$H-NMR: δ(ppm)=1.30 (s, 6H, —CH$_3$), 2.81 (s, 2H, C-1), 4.17 (s, 2H, C-3), 6.84-7.47 (m, 14H, Arom.), 9.40 (s, 1H, —CHO).

EXAMPLE 212

3-(2,2-DIMETHYL-6-(4-PHENOXYPHENYL)-7-PHENYL-2,3-DIHYDRO-1H-PYRROLIZINE-5-YL)-ACRYLIC-ACID ETHYLESTERS (34w)

2 mmoles of 6w dissolved in 5 ml of absolute CH$_3$Cl$_2$ are reacted with the solution of 2 mmoles (0.86 g) of ethoxycarbonyltrimethyltriphenylphosphonium bromide in 4 ml of absolute ethanol and a solution of Na-ethanolate prepared from 6 mmoles (0.14 g) of sodium and 3 ml of absolute ethanol in a manner similar to the procedure for preparing the diphenyl-2,3-dihydro-1H-pyrrolizinyl acrylic-acid esters. Purification is by column chromatography (silica gel, CH$_2$Cl$_2$). The product remains in the form of foam after the eluates have been concentrated.
Yield: 0.33 g (35%).
Melting point: from 69° C.
C$_{32}$H$_{31}$NO$_3$ (477.6).
IR; $\nu_{max}$=1705 (C=O), 1610 (C=C) cm$^{-1}$.
$^1$H-NMR: δ(ppm)=1.28 (t, 3H, J=7 Hz, —O—CH$_2$—CH$_3$), 1.33 (s, 6H, —CH$_3$), 2.86 (s, 2H, C-1), 4.00 (s, 2H, C-3), 4.19 (q, 2H, J=7 Hz, —O—CH$_2$—CH$_3$), 5.92 (AB, 1H, J=16 Hz, =CH—CO—), 6.83-7.44 (m, 14H, Arom.), 7.56 (AB, 1H, J=16 Hz, Pyr—CH=).

EXAMPLE 213

3-(2,2-DIMETHYL-6-(4-PHENOXYPHENYL)-7-PHENYL-2,3-DIHYDRO-1H-PYRROLIZINE-5-YL) ACRYLIC ACID 935w)

0.6 mmoles of 34w dissolved in 30 ml of ethanol are reacted with 6 ml of 10% aqueous KOH n a manner similar to the procedure for saponifying the diphenyl-2,3-dihydro-1H-pyrrolizine-5-yl acrylic-acid ethylesters.
Yield: 0.23 g (85%).
Melting point: 198° C.
C$_{30}$h$_{27}$NO$_3$ (449.5) COMPUTED C 80.2; H 6.05; N 3.1. MEASURED C 79.9; H 6.07; N 2.7.
IR: $\nu_{max}$=3300-2200 (OH), 1675 (C=O), 1590 (C=C) cm$^{-1.}$
$^1$H-NMR (d$_6$-DMSO): δ(ppm)=1.27 (s, 6H, —CH$_3$), 2.83 (s, 2H, C-1), 4.06 (s, 2H, C-3), 5.92 (AB, 1H, J=16.2 Hz, =CH—CO—), 6.86-7.57 (m, 15H, Arom. and Pyr—CH=).

EXAMPLE 214

3-(2,2-DIMETHYL-6-(4-PHENOXYPHENYL)-7-PHENYL-2,3-DIHYDRO-1H-PYRROLIZINE-5-YL) PROPIONIC ACID (27w)

0.3 mmoles of 35w are reacted in the manner of the procedure for hydrogenating the aromatics-substituted 3-(6,7-diphenyl-2,3-dihydro-1H-pyrrolizine-5-yl) acrylic acids. Palladium is used as the catalyst. The product is precipitated by n-hexane.

Yield: 0.10 g (74%).
Melting point: 149° C.
$C_{30}H_{29}NO_3$ (451.6; COMPUTED; C 79.8; H 6.47; N 3.1. MEASURED; C 79.5; H 6.61; N 2.7.

IR: $\nu_{max}$=3300-2400 (OH), 1710 (C=O), 1605 and 1595 (C=C)cm$^{-1}$.

1H-NMR: δ(ppm)=1.29 (s, 6H, —CH$_3$), 2.34-2.63 (m, 2H, —CH$_2$—CO—), 2.77-3.06 (m, 2H, Pyr—CH$_2$—), 2.83 (s, 2H, C-1), 3.69 (s, 2H, C-3), 6.85-7.47 (m, 14H, Arom.).

EXAMPLE 215

2-(2,2-DIMETHYL-6-(4-PHENOXYPHENYL)-7-PHENYL-2,3-DIHYDRO-1H-PYRROLIZINE-5-YL) PROPIONIC-ACID ETHYLESTERS (54a)

2.5 mmoles of 6-(4-phenoxyphenyl)-7-phenyl-2,3-dihydro-1H-pyrrolizine 1w dissolved in 3 ml of absolute toluene are reacted with 4 mmoles (0.51 g) of 2-diazopropionic-acid ethylester dissolved in 3 ml of absolute toluene in a manner similar to the procedure for preparing the diphenyl-2,3-dihydro-1H-pyrrolizinyl aceticacid ethylesters["s.S."201]. Isolation is by means of column chromatography (Al$_2$O$_3$, n-hexane-/ether 9+1). The oily product (0.45 g) remaining after concentration of the eluates is impure. It is reacted further without additional purification.

EXAMPLE 216

2-(2,2-DIMETHYL-6-(4-PHENOXYPHENYL)-7-PHENYL-2,3-DIHYDRO-1H-PYRROLIZINE-5-YL) PROPIONIC ACID (56a)

The impure 54a (0.45 g) dissolved in 10 ml of ethanol is reacted with 5 ml of 10% aqueous KOH in a manner similar to the saponification procedure for the diphenyl-2,3-dihydro-1H-pyrrolizinyl acetic-acid ethylesters. The time of saponification is 90 minutes. Purification is by column chromatography (silica gel, diisopropylether).

Yield: 90 mg.
Melting point: 186° C.
$C_{30}H_{29}NO_3$ (451.6).

IR: $\nu_{max}$=3300-2400 (OH), 1710 (C=O), 1605 and 1595 (C=C) cm$^{-1}$.

1H-NMR: δ(ppm)=1.23 (s, 3H—CH$_3$), 1.32 (s, 3H, —CH$_3$), 1.48 (d, 3H, J=7 Hz, CH$_3$—CH<), 2.72, 2.91 (AB, 2H, J=15.5 Hz, C-1), 3.81 (s, 2H, C-3), 3.96 (z, 1H, J=7 Hz, —CH<), 6.81-7.50 (m, 10H, Arom.).

We claim:

1. A substituted pyrrolizine compound of the formula (I):

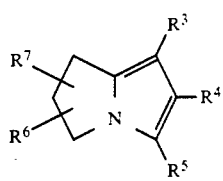

as well as the pharmaceutically compatible salts or esters thereof; wherein two of the residues $R^3$ and $R^4$ and $R^5$ independently from one another represent a phenyl or naphthyl group wherein at least one of said phenyl or naphthyl groups is substituted by one or two residues selected from a halogen atoms, a nitro-, a $C_1$-$C_4$ alkoxy-, a hydroxy, a $C_1$-$C_4$ alkyl- or phenoxy-group and wherein the third of the residues $R^3$, $R^4$ and $R^5$ denotes CO$_2$H, —COSC$_1$-C$_4$—alkyl or A-X, with A being a straight chain or a branched $C_1$-$C_8$-alkylene group which may be interrupted by an oxygen heteroatom or a carbonyl group or said A being a $C_2$-$C_8$ alkenylene group with the proviso that A is not —CH$_2$—when X is OH; and said X being CO$_2$H, SO$_3$H, CHO, OH or SH; and R6 and R$^7$ independently form one another represent a hydrogen atom or a $C_1$-$C_4$ alkyl group.

2. The compound defined in claim 1 wherein two of the residues $R^3$, $R^4$ and $R^5$ represent a phenyl group, and at least one of said phenyl groups is substituted by one or two residues selected from a halogen atom, a $C_1$-$C_4$ alkyl, $C_1$-$C_4$ alkoxy-,hydroxy-, phenoxy and nitro group and the third residue represent A-X, whereby A denotes a $C_1$-$C_8$ alkylene group or a $C_2$-$C_8$ alkenylene group and X represent CO$_2$H.

3. The compound of claim 2 wherein he halogen is fluorine or chlorine.

4. The compound defined in claim 1 having the formula:

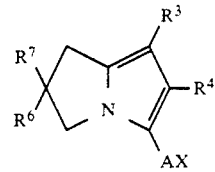

wherein R$^6$ and R$^7$ denote a hydrogen atom or a $C_1$-$C_4$-alkyl group, R$^3$ and R$^4$ independently from one another represent a phenyl group which may be substituted by a halogen atom, A represents a $C_1$-$C_8$-alkyl group and X represents CO$_2$H.

5. The compound defined in claim 4 where R$^3$ and R$^4$ independently from one another represent a phenyl group or a p-chlorophenyl group and where AX represents CH$_2$CO$_2$H.

6. The compound defined in claim 5 where R$^6$ and R$^7$ represent a $C_1$-$C_4$-alkyl group.

7. The compound of claim 6 wherein R$^6$ and R$^7$ are a methyl group.

8. A pharmaceutical composition containing at least one compound defined in claim 1 together with an effective amount of conventional pharmaceutically-compatible inactive substances and/or additives.

* * * * *